United States Patent
Ma

(10) Patent No.: US 9,593,378 B2
(45) Date of Patent: *Mar. 14, 2017

(54) BCR-ABL1 SPLICE VARIANTS AND USES THEREOF

(71) Applicant: Quest Diagnostics Investments Incorporated, Wilmington, DE (US)

(72) Inventor: Wanlong Ma, Aliso Viejo, CA (US)

(73) Assignee: QUEST DIAGNOSTICS INVESTEMENTS INCORPORATED, Wilmington, DE (US)

( * ) Notice: Subject to any disclaimer, the term of this patent is extended or adjusted under 35 U.S.C. 154(b) by 507 days.

This patent is subject to a terminal disclaimer.

(21) Appl. No.: 14/076,324

(22) Filed: Nov. 11, 2013

(65) Prior Publication Data

US 2014/0141427 A1     May 22, 2014

Related U.S. Application Data

(63) Continuation of application No. 12/981,416, filed on Dec. 29, 2010, now Pat. No. 8,603,740.

(51) Int. Cl.
*C12Q 1/68* (2006.01)
*G01N 33/574* (2006.01)

(52) U.S. Cl.
CPC ..... *C12Q 1/6886* (2013.01); *G01N 33/57426* (2013.01); *C12Q 2600/106* (2013.01); *C12Q 2600/136* (2013.01); *C12Q 2600/156* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,798,885 A | 1/1989 | Mason et al. | |
| 4,874,853 A | 10/1989 | Rossi | |
| 4,946,778 A | 8/1990 | Ladner et al. | |
| 4,952,496 A | 8/1990 | Studier et al. | |
| 5,057,410 A | 10/1991 | Kawasaki et al. | |
| 5,963,456 A | 10/1999 | Klein et al. | |
| 6,001,230 A | 12/1999 | Burolla | |
| 6,217,731 B1 | 4/2001 | Kane et al. | |
| 6,849,400 B1 | 2/2005 | Harvey et al. | |
| 6,939,671 B2 | 9/2005 | Kopreski | |
| 7,521,213 B2 | 4/2009 | Hantash | |
| 7,585,626 B1 | 9/2009 | Hantash et al. | |
| 2003/0158105 A1 | 8/2003 | Sawyers et al. | |
| 2005/0202519 A1 | 9/2005 | Barthe et al. | |
| 2006/0269956 A1 | 11/2006 | Sawyers et al. | |
| 2010/0113470 A1 | 5/2010 | Albitar | |

FOREIGN PATENT DOCUMENTS

| | | |
|---|---|---|
| EP | 0 367 76 A2 | 9/1981 |
| EP | 0 117 060 | 8/1984 |
| EP | 0 117 058 | 9/1989 |
| GB | 2 211 504 A | 7/1989 |
| WO | WO-2009/061890 | 5/2009 |

OTHER PUBLICATIONS

Alderborn et al., "Determination of Single-Nucleotide Polymorphisms by Real-time Pyrophosphate DNA Sequencing," Genome Res. (2000), 10:1249-1265.
Caceres et al, "Alternative splicing: multiple control mechanisms and involvement in human disease," Trends in Genetics 2002 18:186-193.
Chang et al., "Phenotypic expression in *E. coli* of a DNA sequence coding for mouse dihydrofolate reductase," Nature (1978), 275:617-624.
Cote et al., "Generation of human monoclonal antibodies reactive with cellular antigens," Proc. Natl. Acad. Sci. (1983), 80:2026-2030.
deBoer et al., "The tac promoter: A functional hybrid derived from the trp and lac promoters," Proc. Natl. Acad. Sci. USA, vol. 80, pp. 21-25, Jan. 1983.
Drexler, H.G., The Leukemia-Lymphoma Cell Line Factsbook (2000), Academic Press.
Duffaud et al., "Expression and Secretion of Foreign Proteins in *Escherichia coli*," Meth. in Enzymology, 153:492-507, 1987.
GenBank Accession No. U07563.1, Human Proto-oncogene tyrosine-protein kinase (ABL) gene, exon 1a and exons 2-10, complete cds, printed Aug. 8, 2012. 33 pages.
Gething et al., "Cell-surface expression of influenza haemagglutinin from a cloned DNA of the RNA Gene," Nature (1981), 293:620-625.
Goeddel et al., "Direct expression in *Escherichia coli* of a DNA sequence coding for human growth hormone," Nature (1979), 281:544-548.
Gruber et al., "A novel Bcr-Abl splice isoform is associated with the L248V mutation in CML patients with acquired resistance to imatinib," Leukemia, Nov. 2006 vol. 20 No. 11, pp. 2057-2060.
H. Erlich, PCR Technology, Principles and Application for DNA Amplifications, 1989.
Heid, et al., "Real Time Quantitative PCR," Genome Res 6:986-994, 1996.
Hitzeman et al., "Isolation and Characterization of the Yeast 3-Phosphoglycerokinase Gene (PGK) by and Immunological Screening Technique," J. Biol. Chem, (1980), 255:12073-12080.
Holland, et al., "Isolation and Indentification of Yeast Messenger Ribonucleic Acids Coding for Enolase, Glyceraldehyde-3-Phosphate Dehydrogenase and Phosphoglycerate Kinase," Biochemistry (1978), 17:4900-4907.
Huse et al., "Generation of a Large Combinatorial Library of the Immunoglobulin Repertoire in Phage Lambda," Science, 1989; 246:1275-1281.
Kanehisa, M., "Use of Statistical Criteria for Screening Potential Homologies in Nucleic Acid Sequences," Polynucleotides Res. (1984), 12(1):203-213.
Kingsman et al., "Replication in *Saccharomyces cerevisiae* of Plasmid pBR313 Carrying DNA from the Yeast trpl Region," Gene (1979), 7:141-152; Elsevier/North-Holland Biomedical Press, Amsterdam—Printed in the Netherlands.

(Continued)

*Primary Examiner* — Juliet Switzer
(74) *Attorney, Agent, or Firm* — Foley & Lardner LLP

(57) ABSTRACT

The present invention is based on BCR-ABL1 splice variants which result from insertion and/or truncation of the bcr-abl1 transcript and the finding that these variants provide resistance to kinase domain inhibitors such as imatinib, nilotinib and dasatinib.

11 Claims, 11 Drawing Sheets

(56) References Cited

OTHER PUBLICATIONS

Kohler et al., "Continuous cultures of fused cells secreting antibody of predefined specificity," Nature (1975), 256:495-497.

Kozbor et al., "The Production of Monoclonal antibodies from human lymphocytes," Immunology Today (1983), 4(3):72-79.

Mantei et al., "Rabbit β-globin mRNA Production in mouse L cells transformed with cloned rabbit β-globin chromosomal DNA," Nature, Sep. 6, 1979, 281:40-46.

Marasco et al. (ed.), Intracellular Antibodies: Research and Disease Applications, Springer-Verlag New York, Inc. (1998) (ISBN: 3540641513).

McKenzie et al., "Mutants of the Formyltetrahydrofolate interconversion pathway of *Saccharomyces cerevisiae*," Genetics (1977), 86:85-102.

Morrison et al., "Chimeric human antibody molecules: Mouse antigen-binding domains with human constant region domains," Proc. Natl. Acad. Sci. USA Nov. 1984, 81:6851-6855.

Mosmann, Tim, "Rapid Colorimetric Assay for Cellular Growth and Survival: Application to Proliferation and Cytotoxicity Assays," J. Immunol. Meth. 1983; 65:55-63.

Mulligan et al., "Synthesis of rabbit β-globin in cultured monkey kidney cells following infection with a SV40 β-globin recombinant genome," Nature, Jan. 11, 1979, vol. 277:108-114.

NCBI GenBank Accession No. AB069693, *Homo Sapiens* mRNA for bcr/abl e8a2 fusion protein, partial cds; http://www.ncbi.nlm.nih.gov/nuccore/AB069693.1?report=gbwithparts&log$=seqview, printed Aug. 8, 2012, 2 pages.

NCBI GenBank Accession No. AF113911, *Homo sapiens* BCR-ABL1 e1a2 chimeric protein (BCR/ABL fusion) mRNA, partial cds; http://www.ncbi.nlm.nih.gov/nuccore/AF113911.1?report=gbwithparts&log$=seqview, printed Aug. 8, 2012 2 pages.

NCBI GenBank Accession No. AF251769, *Homo sapiens* bcr/abl e1-a3 chimeric fusion protein (BCR/ABLe1-a3) mRNA, partial cds; http://www.ncbi.nlm.nih.gov/nuccore/AF251769.1?report=gbwithparts&log$=seqview, printed Aug. 8, 2012 1 page.

NCBI GenBank Accession No. AF487522, *Homo sapiens* BCRe18/ABL1e3 fusion protein (BCR/ABL fusion) mRNA, partial cds; http://www.ncbi.nlm.nih.gov/nuccore/AF487522.1?report=gbwithparts&log$=seqview, printed Aug. 8, 2012 1 page.

NCBI GenBank Accession No. AY789120, *Homo sapiens* BCR/ABL fusion mRNA sequence; http://www.ncbi.nlm.nih.gov/nuccore/AY789120.1?report=gbwithparts&log$=seqview, printed Aug. 8, 2012 1 page.

NCBI GenBank Accession No. DQ898313, *Homo sapiens* isolate e1a4 BCR/ABL fusion protein (BCR/ABL fusion) mRNA, partial cds, alternatively spliced; http://www.ncbi.nlm.nih.gov/nuccore/dq898313, printed Aug. 8, 2012 2 pages.

NCBI GenBank Accession No. DQ898314, *Homo sapiens* isolate e13a4 BCR/ABL fusion protein (BCR/ABL fusion) mRNA, partial cds, alternatively spliced; http://www.ncbi.nlm.nih.gov/nuccore/DQ898314.1?report=gbwithparts&log$=seqview, printed Aug. 8, 2012 2 pages.

NCBI GenBank Accession No. DQ898315, *Homo sapiens* isolate e14a4 BCR/ABL fusion protein (BCR/ABL fusion) mRNA, partial cds alternatively spliced; http://www.ncbi.nlm.nih.gov/nuccore/DQ898315.1?report=gbwithparts&log$=seqview, printed Aug. 8, 2012 2 pages.

NCBI GenBank Accession No. DQ912588. *Homo sapiens* BCR/ABL fusion protein e1a5 (BCR/ABL fusion) mRNA, partial cds, alternatively spliced; http://www.ncbi.nlm.nih.gov/nuccore/DQ912588.1?report=gbwithparts&log$=seqview, printed Aug. 8, 2012 1 page.

NCBI GenBank Accession No. DQ912589, *Homo sapiens* BCR/ABL fusion protein e13a5 (BCR/ABL fusion) mRNA, partial cds, alternatively spliced; http://www.ncbi.nlm.nih.gov/nuccore/DQ912589.1?report=gbwithaparts&log$=seqview, printed Aug. 8, 2012 1 page.

NCBI GenBank Accession No. DQ912590, *Homo sapiens* BCR/ABL fusion protein e14a5 (BCR/ABL fusion) mRNA, partial cds, alternatively spliced; http://www.ncbi.nlm.nih.gov/nuccore/DQ912590.1?report=gbwithparts&log$=seqview, printed Aug. 8, 2012 1 page.

NCBI GenBank Accession No. EF158045, *Homo sapiens* BCR/ABL p210 fusion protein (BCR/ABL fusion) mRNA, partial cds; http://www.ncbi.nlm.nih.gov/nuccore/EF158045.1?report=gbwithparts&log$=seqview, printed Aug. 8, 2012 1 page.

NCBI GenBank Accession No. EF423615, *Homo sapiens* BCR/ABL fusion protein (BCR/ABL fusion) mRNA, partial cds; http://www.ncbi.nlm.nih.gov/nuccore/EF423615?report=gbwithparts&log$=seqview, printed Aug. 8, 2012 1 page.

NCBI GenBank Accession No. EU216058, *Homo sapiens* BCR/ABL fusion protein isoform X1 (BCR/ABL fusion) mRNA, complete cds; http://www.ncbi.nlm.nih.gov/nuccore/EU216058.1?report=gbwithparts&log$=seqview, printed Aug. 8, 2012 2 pages.

NCBI GenBank Accession No. EU216059, *Homo sapiens* BCR/ABL fusion protein isoform X2 (BCR/ABL fusion) mRNA, complete cds; http://www.ncbi.nlm.nih.gov/nuccore/EU216059.1?report=gbwithparts&log$=seqview, printed Aug. 8, 2012 2 pages.

NCBI GenBank Accession No. EU216060, *Homo sapiens* BCR/ABL fusion protein isoform X3 (BCR/ABL fusion) mRNA, complete cds; http://www.ncbi.nlm.nih.gov/nuccore/Eu216060, printed Aug. 8, 2012 3 pages.

NCBI GenBank Accession No. EU216061, *Homo sapiens* BCR/ABL fusion protein isoform X4 (BCR/ABL fusion) mRNA, complete cds; http://www.ncbi.nlm.nih.gov/nuccore/Eu216061, printed Aug. 8, 2012 2 pages.

NCBI GenBank Accession No. EU216062, *Homo sapiens* BCR/ABL fusion protein isoform X5 (BCR/ABL fusion) mRNA, complete cds; http://www.ncbi.nlm.nih.gov/nuccore/Eu216062, printed Aug. 8, 2012 2 pages.

NCBI GenBank Accession No. EU216063, *Homo sapiens* BCR/ABL fusion protein isoform X6 (BCR/ABL fusion) mRNA, complete cds; http://www.ncbi.nlm.nih.gov/nuccore/Eu216063, printed Aug. 8, 2012 2 pages.

NCBI GenBank Accession No. EU216064, *Homo sapiens* BCR/ABL fusion protein isoform X7(BCR/ABL fusion) mRNA, complete cds; http://www.ncbi.nlm.nih.gov/nuccore/Eu216064, printed Aug. 8, 2012 2 pages.

NCBI GenBank Accession No. EU216065, *Homo sapiens* BCR/ABL fusion protein isoform X8 (BCR/ABL fusion) mRNA, complete cds; http://www.ncbi.nlm.nih.gov/nuccore/Eu216065, printed Aug. 8, 2012 2 pages.

NCBI GenBank Accession No. EU216066. *Homo sapiens* BCR/ABL fusion protein isoform X9 (BCR/ABL fusion) mRNA, complete cds; http://www.ncbi.nlm.nih.gov/nuccore/Eu216066, printed Aug. 8, 2012 3 pages.

NCBI GenBank Accession No. EU216067, *Homo sapiens* BCR/ABL fusion protein isoform Y1 (BCR/ABL fusion) mRNA, complete cds; http://www.ncbi.nlm.nih.gov/nuccore/Eu216067, printed Aug. 8, 2012 2 pages.

NCBI GenBank Accession No. EU216068, *Homo sapiens* BCR/ABL fusion protein isoform Y2 (BCR/ABL fusion) mRNA, complete cds; http://www.ncbi.nlm.nih.gov/nuccore/Eu216068, printed Aug. 8, 2012 2 pages.

NCBI GenBank Accession No. EU216069, *Homo sapiens* BCR/ABL fusion protein isoform Y3 (bcr/ABL fusion) mRNA, complete cds; http://www.ncbi.nlm.nih.gov/nuccore/Eu216069, printed Aug. 8, 2012 2 pages.

NCBI GenBank Accession No. EU216070, *Homo sapiens* BCR/ABL fusion protein isoform Y4 (BCR/ABL fusion) mRNA, complete cds; http://www.ncbi.nlm.nih.gov/nuccore/Eu216070; printed Aug. 8, 2012 2 pages.

NCBI GenBank Accession No. EU216071, *Homo sapiens* BCR/ABL fusion protein isoform Y5 (BCR/ABL fusion) mRNA, complete cds; http://www.ncbi.nlm.nih.gov/nuccore/Eu216071, printed Aug. 8, 2012 3 pages.

NCBI GenBank Accession No. EU236680, *Homo sapiens* BCR/ABL b3a3 fusion protein (BCR/ABL fusion) mRNA, partial cds; htt://www.ncbi.nlm.nih.gov/nuccore/eu236680, printed Aug. 8, 2012 2 pages.

(56) References Cited

OTHER PUBLICATIONS

NCBI GenBank Accession No. M14752, Human c-abl gene, complete cds; http://www.ncbi.nlm.nih.gov/nuccore/m14752, printed Aug. 8, 2012 2 pages.
NCBI GenBank Accession No. M15025, Human BCR/ABL mRNA (product of translocation t(22q11;9q34)), 5'end; www.ncbi.nlm.nih.gov/nuccore/m15025, printed Aug. 8, 2012, 2 pages.
NCBI GenBank Accession No. M17541, Human bcr/abl fusion protein (product of translocation t(22q11; 9q34)), exons 1 and 2; http://www.ncbi.nlm.nih.gov/nuccore/m17541, printed Aug. 8, 2012 1 page.
NCBI GenBank Accession No. M17542, Human bcr/abl protein gene (product of tranlocation t(22q11; 9q34)), exons 1 and 2, http://www.ncbi.nlm.nih.gov/nuccore/m17542, printed Aug. 8, 2012 1 page.
NCBI GenBank Accession No. M30829, Human bcr/abl fusion protein mRNA, partial cds, clone K28; http://www.ncbi.nlm.nih.gov/nuccore/m30829, printed Aug. 8, 2012 1 page.
NCBI GenBank Accession No. M30832, Human bcr/abl fusion protein, partial cds, clone E3; http://www.ncbi.nlm.nih.gov/nuccore/m30832, printed Aug. 8, 2012, 1 page.
NCBI GenBank Accession No. S72478, BCR . . . ABL {b3/a3 junction, translocation breakpoint} [human, Japanese CML patient 1 and ALL patient 2, peripheral blood, monoculear cells, mRNA Mutant, 3 genes, 140 nt]; http://www.ncbi.nlm.nih.gov/nuccore/s72478, printed Aug. 8, 2012 1 page.
NCBI GenBank Accession No. S72479, BCR . . . ABL {e1/a3 junction, translocation breakpoint} [human, Japanese All patient 3, bone marow, mononuclear cells, mRNA Mutant, 3 genes, 131 nt]. http://www.ncbi.nlm.nih.gov/nuccore/s72479, printed Aug. 8, 2012 1 page.
NCBI GenBank Accession Nos. EU216072, *Humo sapiens* BCR/ABL fusion protein isoform Y6 (BCR/ABL fusion) mRNA, complete cds; http://www.ncbi.nlm.nih.gov/nuccore/eu216072, printed Aug. 8, 2012 2 pages.
NCBI Protein Database Accession No. AAA35594, BCR-ABL protein, partial (*Homo sapiens*); http:www.ncbi.nlm.nih.gov/protein/AAA35594.1?report=gpwithparts&log$=seqview, printed Aug. 8, 2012 1 page.
NCBI Protein Database Accession No. ABX82702, BCR/ABL fusion protein isoform X3 [*Homo Sapiens*]; http://www.ncbi.nlm.nih.gov/protein/abx82702, printed Aug. 8, 2012, 2 pages.
NCBI Protein Database Accession No. ABX82708, BCR/ABL fusion protein isoform X9 [*Homo sapiens*]; http://www.ncbi.nlm.nih.gov/protein/abx82708, printed Aug. 8, 2012, 2 pages.
Neuberger et al., "Recombinant antibodies possessing novel effector functions," Nature, Dec. 13, 1984, 312:604-608.
Okayama, "High-Efficiency Cloning of Full-Lenghth DNA," Mol. Cell. Biol. Feb. 1982, vol. 2:161-170.
Phillips G.J., "Green fluorescent protein—a bright idea for the study of bacterial protein localization," FEMS Microbiol. Lett. 2001; 204(1):9-18.
Sambrook, et al., Molecular Cloning: A Laboratory Manual (1989), Second Edition, Cold Spring Harbor Press, Plainview, NY.
Sanger et al., "DNA sequencing with chain-terminating inhibitors," PNAS USA, Dec. 1977, 74(12):5463-5467.
Stinchcomb et al., "Isolation and Characterisation of a yeast chromosomal replicator," Nature, Nov. 1979, 282:39-43.
Stoilov et al., "Defects in Pre-mRNA Processing as Causes of and Predisposition to Diseases," DNA and Cell Biology, 2002 21(11):803-818.
Sun et al., "Modulation of the Cytotoxicity of 3'-Azido-3'-deoxythymidine and Methotrexate after Transduction of Folate Receptor cDNA into Human Cervical Carcinoma: Identification of a Correlation between Folate Receptor Expression and Thymidine Kinase Activity," Cancer Res. Feb. 15, 1999; 59:940-946.
Takeda et al., "Construction of chimaeric processed immunoglobulin genes containing mouse variable and human constant region sequences," Nature, Apr. 4, 1985, 314:452-454.

Tyagi et al., "Multicolor molecular beacons for allele discrimination," Nature Biotechnology, Jan. 1998, 16:49-53.
Urlaub et al., "Isolation of Chinese hamster cell mutants deficient in dihydrofolate reductase activity," Proc. Natl Acad. Sci. USA, Jul. 1980, pp. 4216-4220, vol. 77, No. 7.
Wong et al., "Human GM-CSF: Molecular Cloning of the Complementary DNA and Purification of the Natural and Recombinant Proteins," Science, 1985; 228:810-815.
Wong et al., "The BCR-ABL Story: Bench to Bedside and back," Annu. Rev. Immunol. 2004; 22:247-306.
Wu et al., "Alternatively Spliced Genes," Encyclopedia of Molecular and Cell Biology and Molecular Medicine, vol. 1, 2nd ed., 125-177 (2004).
Zimmermann et al., "A simplified protocol for fast plasmid DNA sequencing," Nucleic Acids Res. vol. 18, No. 4, p. 1067, Submitted Jan. 19, 1990, © 1990 Oxford University Press.
Abravaya, et al., Detection of point mutations with a modified ligase chain reaction (Gap-LCR). Nucleic Acids Research 23:675-682, (1995).
Bradeen et al., Comparison of imatinib mesylate, dasatinib (BMS-354825), and nilotinib (AMN107) in an N-ethyl-N-nitrosourea (ENU)-based mutagenesis screen: high efficacy of drug combinations, Blood, 108:2332-2338 (2006).
Branford et al., Detection of BCR-ABL mutations in patients with CML treated with imatinib is virtually always accompanied by clinical resistance, and mutations in the ATP phosphate-binding loop (P-loop) are associated with a poor prognosis, Blood, 102:276-283 (2003).
Evans et al, Pharmacogenomics: Translating Functional Genomics into Rational Therapeutics Science vol. 286:487-491 (1999).
Kievits, et al., NASBA™ isothermal enzymatic in vitro nucleic acid amplification optimized for the diagnosis of HIV-1 infection. J Virological Methods 35:273-286, (1991).
Quintas-Cardama et al, Phase I/II study of subcutaneous homoharringtonine in patients with chronic myeloid leukemia who have failed prior therapy, Cancer, 109(2):248-255 (2006).
Tokarski et al, The structure of dasatinib (BMS-354825) bound to activated ABL kinase domain elucidates its inhibitory activity against imatinib-resistant ABL mutants, Cancer Research, 66(11):5790-5797 (2006).
Urdea, et al., Direct and quantitative detection of HIV-1 RNA in human plasma with a branched DNA signal amplification assay. AIDS 7 (suppl 2):S11-S 14, (1993).
US Office Action dated Mar. 14, 2012 in U.S. Appl. No. 12/472,319.
US Office Action dated Jul. 6, 2011 in U.S. Appl. No. 11/301,272.
Azam et al., Activity of dual SRC-ABL inhibitors highlights the role of BCR/ABL kinase dynamics in drug resistance, PNAS, 103(24):9244-9249 (2006).
Branford et al., High frequency of point mutations clustered within the adenosine triphosphate-binding region of BCR/ABL in patients with chronic myeloid leukemia or Ph-positive acute lymphoblastic leukemia who develop imatinib (STI571) resistance, Blood, 99: 3472-3475 (2002).
Burgess et al., Comparative analysis of two clinically active BCR-ABL kinase inhibitors reveals the role of conformation-specific binding in resistance, PNAS, 102(9):3395-3400 (2005).
Capdeville et al., Glivec (STI571, Imatinib), a Rationally Developed, Targeted Anticancer Drug, Nat. Rev. Drug Discov., 1:493 (2002).
Catovsk D., "Ph1 positive acute leukemia and chronic granulocytic leukemia: one or two disease." Br. J. Haematol 42: 493-498 (1979).
Chu et al., Dasatinib in Chronic Myelogenous Leukemia, N. Engl. J. Med., 355: 1062-1064(2006).
Clark S. S. et al., "Unique forms of the abl tryrosine kinase distinguish PH-positive CML from PH-positive ALL." Science 235:85-88, (1987).
Cross, et al., Competitive polymerase chain reaction to estimate the number of BCR-ABL transcripts in chronic myeloid leukemia patients after bone marrow transplantation. Blood 82: 1929-36, (1993).
Curvo et al., Leukemia Research, (2008), 32:508-510.

(56) References Cited

OTHER PUBLICATIONS

Deininger et al., The Tyrosine Kinase Inhibitor CGP57148B Selectively Inhibits the Growth of BCR-ABL-Positive Cells, Blood, 90: 3691-3698 (1997).
Deininger, et al., The development of imatinib as a therapeutic agent for chronic myeloid leukemia. Blood 105:2640-53 (2005).
Donato, N.J., BCR-ABL independence and LYN kinase overexpression in chronic myelogenous leukemia cells selected for resistance to STI571, Blood, 101: 690-698 (2003).
Eder et al, "Monitoring of BCR-ABL expression using Real-time RT-PCR in CML after bone marrow or peripheral blood stem cell transplantation." Leukemia 13:1383-1389 (1999).
Elefanty et al., bcr-abl, the hallmark of chronic myeloid leukaemia in man, induces multiple haemopoietic neoplasms in mice, EMBO J., 9(4):1069-1078 (1990).
Emig et al. Accurate and rapid analysis of residual disease in patients with CML using specific fluorescent hybridization probes for real time quantitative RT-PCR. Leukemia, 13:1825-1832, 1999.
Ernst et al, Haematologica, (2008), 93(2):186-192.
Gorre et al., BCR-ABL point mutants isolated from patients with imatinib mesylate-resistant chronic myeloid leukemia remain sensitive to inhibitors of the BCR-ABL chaperone heat shock protein 90, Blood, 100: 3041-3044 (2002).
Gorre et al., Clinical Resistance to STI-571 Cancer Therapy Caused by BCR-ABL Gene Mutation or Amplification, Science, 293: 876-880 (2001).
Gruber et al, Leukemia, (2006), 20(11):2057-2060.
Gumireddy et al., A non-ATP-competitive inhibitor of BCR-ABL overrides imatinib resistance. PNAS, 102:1992, 2005.
Hariharan et al., cDNA sequence for human BCR, the gene that translocates to the abl oncogene in chronic myeloid leukemia. EMBO J. 6(1):115-119 (1987).
Hochhaus et al., Molecular and chromosomal mechanisms of resistance to imatinib (STI571) therapy, Leukemia. 16: 2190-2196 (2002).
Hochhaus, et al., Hematologic and Cytogenic Response Dynamics to Nilotinib (AMN107) Depend on the Type of BCR-ABL Mutations in Patients with Chronic Myelogenous Leukemia (CML) after Imatinib Failure, Blood, 108: 225a (2006).
Hughes et al., Monitoring CML patients responding to treatment with tyrosine kinase inhibitors: review and recommendations for harmonizing current methodology for detecting BCR-ABL transcripts and kinase domain mutations and for expressing results, Blood, 108: 28-37 (2006).
International Search Report dated Apr. 15, 2011 in application PCT/US2010/058987.
International Search Report dated Nov. 8, 2010 in application PCT/US2010/50539.
Kantarjian, et al., Quantitative polymerase chain reaction monitoring of BCR-ABL during therapy with imatinib mesylate (STI571; gleevec) in chronic-phase chronic myelogenous leukemia. Clin. Cancer Res. 9, 160-6 (2003).
Kawasaki et al., "Diagnosis of chronic myelogenous and acute lymphocytic by detection of leukemia-specific mRNA sequences in vitro." Proc. Natl. Acad. Sci USA 85: 5698-5702 (1988).
Klein et al, Oncogene, (2006), 25(7):1118-1124.
Konopka J.B. et al., An alternative of the human c-abl protein in K562 leukemia cells unmasks associated Tyrosine kinase activity. Cell 37:1035-1042 (1984).
Kreuzer et al., "Applicability of an Absolute Quantitative Procedure to Monitor Intra-individual bcr/abl Transcript Kinetics in Clinical Samples from Chronic Myelogenous Leukemia Patients" Int. J. Cancer: 86:741-746 (2000).
Kuroda et al., Bim and Bad mediate imatinib-induced killing of BCR/ABL+ leukemic cells, and resistance due to their loss is overcome by a BH3 mimetic, Proc. Natl. Acad. Sci., U.S.A. 103:14097 (2006).
Kurzrock et al., The Molecular Genetics of Philadelphia Chromosome-Positive Leukemias, N. Engl. J. Med., 319: 990-998 (1988).
Laudadio et al., Consultations in Molecular Diagnostics, An Intron-Derived Insertion/Truncation Mutation in the BCR-ABL Kinase Domain in Chronic Myeloid Leukemia Patients Undergoing Kinase Inhibitor Therapy, J. Mol. Diag., 10(2): 177-180 (2008).
Lee et al., BCR-ABL alternative splicing as a common mechanism for imatinib resistance: evidence from molecular dynamics simulations, Mol. Cancer Ther. 7(12):3834-3841 (2008).
Lerma et al., Novel compounds with antiproliferative activity against imatinib-resistant cell lines, Mol. Cancer Ther., 6(2): 655-66 (2007).
Levinson et al., A Src-Like Inactive Conformation in the Abl Tyrosine Kinase Domain, PLoS Biol., 4: e144 (2006).
Lin et al., Proliferation and apoptosis in acute and chronic leukemias and myelodysplastic syndrome, Leuk Res., 26(6):551-9 (2002).
Lozzio, C.B. and Lozzio, B.B., Human chronic myelogenous leukemia cell-line with positive Philadelphia chromosome, Blood, 45(3):321-334 (1975).
Ma et al, Three novel alternative splicing mutations in BCR-ABL 1 detected in CML patients with resistance to kinase inhibitors, presented at 51st ASH annual meeting and exposition (2009).
Ma et al., BCR-ABL Truncation due to Premature Translation Termination as a Mechanism of Resistance to Kinase Inhibitors, Acta Haematol., 121:27-31 (2009).
Mahon, F.X., Blood, Selection and characterization of BCR-ABL positive cell lines with differential sensitivity to the tyrosine kinase inhibitor STI571: diverse mechanisms of resistance, 96:1070-1079 (2000).
Manley, P.W., Imatinib: a selective tyrosine kinase inhibitor, Eur. J. Cancer, 38: S19-S27 (2002).
Melo, J.V. & Chuah, C., Resistance to imatinib mesylate in chronic myeloid leukaemia, Cancer Lett., 249:121-132 (2007).
Mensink et al., Quantitation of minimal residual diseases in Philadelphia chromosome positive chronic myeloid leukemia patients using real time quantitative PCR. British J. Haematology 102:768-774 (1998).
Nagar et al., Crystal Structures of the Kinase Domain of c-Abl in Complex with the Small Molecule Inhibitors PD173955 and Imatinib (STI-571), Cancer Res., 62: 4236-4243 (2002).
Nagar, B., Structural Basis for the Autoinhibition of C-Abl Tyrosine Kinase, Cell, 112: 859-871 (2003).
O'Hare et al., Combined Abl Inhibitor Therapy for Minimizing Drug Resistance in Chronic Myeloid Leukemia: Src/Abl Inhibitors Are Compatible with Imatinib, Clin. Cancer Res., 11(19):6987-6993 (2005).
O'Hare et al., Bcr-Abl kinase domain mutations, drug resistance, and the road to a cure for chronic myeloid leukemia, Blood, 110:2242-2249 (2007).
O'Hare, et al., AMN107: tightening the grip of imatinib. Cancer Cell 7:117-9 (2005).
Ren et al., Abl protein-tyrosine kinase selects the Crk adapter as a substrate using SH3-binding sites, Genes Dev., 8(7): 783-95 (1994).
Rogers, et al., Relative increase in leukemia-specific DNA in peripheral blood plasma from patients with acute myeloid leukemia and myelodysplasia. Blood 103, 2799-2801 (2004).
Rowley, J.D., A New Consistent Chromosomal Abnormality in Chronic Myelogenous Leukaemia identified by Quinacrine Fluorescence and Giemsa Staining, Nature, 243: 290-3 (1973).
Shah et al., Sequential ABL kinase inhibitor therapy selects for compound drug-resistant BCR-ABL mutations with altered oncogenic potency, J. Clin. Invest., 117:2562-2569 (2007).
Shtivelman et al., "Alternative splicing of RNAs transcribed from the human abl gene and from the bcr-abl fused gene." Cell, 47:277-284 (1986).
Sooknanan, et al., Detection and direct sequence identification of BCR-ABL mRNA in Ph+ chronic myeloid leukemia. Experimental Hematology 21:1719-1724, 1993.
Stroun, et al., Neoplastic characteristics of the DNA found in the plasma of cancer patients. Oncology 46:318-322, 1989.
Thomazy et al., Use of plasma RNA for real-time quantitative RT-PCR to monitor imatinib therapy in patients with chronic myeloid leukemia, Blood (ASH Annual Meeting Abstracts), 104: Abstract 1099, 2004.
US Office Action dated Jan. 8, 2009 in U.S. Appl. No. 11/301,272.

(56) References Cited

OTHER PUBLICATIONS

US Office Action dated May 11, 2011 in U.S. Appl. No. 12/472,319.
US Office Action dated Nov. 12, 2009 in U.S. Appl. No. 11/301,272.
US Office Action dated Dec. 6, 2010 in U.S. Appl. No. 12/472,319.
US Office Action dated Apr. 29, 2008 in U.S. Appl. No. 11/301,272.
Volpe et al, Cancer Res, (2007), 67(11):5300-5307.
Weisberg et al., AMN107 (nilotinib): a novel and selective inhibitor of BCR-ABL, Br. J. Cancer, 94:1765-1769 (2006).
Weisberg et al., Beneficial effects of combining nilotinib and imatinib in preclinical models of BCR-ABL + leukemias, Blood, 109:2112-2120 (2007).
Wertheim, et al., Blood, (2003), 102:2220-2228.
Office Action issued on Feb. 9, 2013 in U.S. Appl. No. 12/981,416.
Notice of Allowance issued on Aug. 9, 2013 in U.S. Appl. No. 12/981,416.
Office Action issued on Jan. 16, 2014 in U.S. Appl. No. 13/512,945.
Office Action issued on Jan. 28, 2014 in U.S. Appl. No. 12/892,679.
Mummidi et al., "Evolution of Human and Non-human Primate CC Chemokine Receptor 5 Gene and mRNA," The Journal of Biological Chemistry, vol. 275, No. 25, pp. 18946-18961, Jun. 23, 2000.
Jüppner, "Functional Properties of the PTH/PRHrP Receptor," Bone, vol. 17, No. 2, pp. 39S-42S, Aug. 1995.
Bolufer et al., "Rapid quantitative detection of BCR-ABL transcripts in chronic myeloid leukemia patients by real-time reverse transcriptase polymerase-chain reaction using fluorescently labeled probes," Haematologica, vol. 85, pp. 1248-1254, Dec. 2000.

FIG. 1

```
   1 aaaatgttgg agatctgcct gaagctggtg ggctgcaaat ccaagaaggg gctgtcctcg
  61 tcctccagct gttatctgga agaagccctt cagcggccag tagcatctga ctttgagcct
 121 cagggtctga gtgaagccgc tcgttggaac tccaaggaaa accttctcgc tggacccagt
 181 gaaaatgacc ccaaccttt  cgttgcactg tatgattttg tggccagtgg agataacact
 241 ctaagcataa ctaaaggtga aaagctccgg gtcttaggct ataatcacaa tggggaatgg
 301 tgtgaagccc aaaccaaaaa tggccaagc  tgggtcccaa gcaactacat cacgccagtc
 361 aacagtctgg agaaacactc ctggtaccat gggcctgtgt cccgcaatgc cgctgagtat
 421 ctgctgagca gcgggatcaa tggcagcttc ttggtgcgtg agagtgagag cagtcctggc
 481 cagaggtcca tctcgctgag atacgaaggg agggtgtacc attacaggat caacactgct
 541 tctgatggca agctctacgt ctcctccgag agccgcttca acaccctggc cgagttggtt
 601 catcatcatt caacggtggc cgacgggctc atcaccacgc tccattatcc agccccaaag
 661 cgcaacaagc ccactgtcta tggtgtgtcc cccaactacg acaagtggga gatggaacgc
 721 acggacatca ccatgaagca caagctgggc ggggccagt  acgggaggt  gtacgaggc
 781 gtgtggaaga aatacagcct gacggtggcc gtgaagacct tgaaggagga caccatggag
 841 gtggaagagt tcttgaaaga agctgcagtc atgaaagaga tcaaacaccc taacctggtg
 901 cagctccttg gggtctgcac ccgggagccc ccgttctata tcatcactga gttcatgacc
 961 tacgggaacc tcctggacta cctgagggag tgcaaccggc aggaggtgaa cgccgtggtg
1021 ctgctgtaca tggccactca gatctcgtca gccatggagt acctggagaa gaaaaacttc
1081 atccacagag atcttgctgc ccgaaactgc ctggtagggg agaaccactt ggtgaaggta
1141 gctgattttg gcctgagcag gttgatgaca ggggacacct acacagccca tgctggagcc
1201 aagttcccca tcaaatggac tgcaccgag  agcctggcct acaacaagtt ctccatcaag
1261 tccgacgtct gggcatttgg agtattgctt tgggaaattg ctacctatgg catgtcccct
1321 tacccgggaa ttgacctgtc ccaggtgtat gagctgctag agaaggacta ccgcatggag
1381 cgcccagaag gctgcccaga gaaggtctat gaactcatgc gagcatgttg gcagtggaat
1441 ccctctgacc ggccctcctt tgctgaaatc caccaagcct ttgaaacaat gttccaggaa
1501 tccagtatct cagacgaagt ggaaaaggag ctggggaaac aaggcgtccg tggggctgtg
1561 agtaccttgc tgcaggcccc agagctgccc accaagacga ggacctccag gagagctgca
1621 gagcacagag acaccactga cgtgcctgag atgcctcact ccaagggcca gggagagagc
1681 gatcctctgg accatgagcc tgccgtgtct ccattgctcc ctcgaaaaga gcgaggtccc
1741 ccggagggcg gcctgaatga agatgagcgc cttctcccca aagacaaaaa gaccaacttg
1801 ttcagcgcct tgatcaagaa gaagaagaag acagccccaa cccctcccaa acgcagcagc
1861 tccttccggg agatggacgg ccagccggag cgcagaggqg ccggcgagga agagggccga
1921 gacatcagca acggggcact ggctttcacc cccttggaca cagctgaccc agccaagtcc
1981 ccaaagccca gcaatggggtc tggggtcccc aatggagtcc tccgggagtc cgggggctca
2041 ggcttccggt ctccccacct gtggaagaag tccagcacgc tgaccagcag ccgcctagcc
2101 accggcgagg aggagggcgg tgcagctcc  agcaagcgct tctgcgctc  ttgctccgcc
2161 tcctgcgttc cccatggggc caaggacacg gagtggaggt cagtcacgct gcctcgggac
2221 ttgcagtcca cgggaagaca gtttgactcg tccacatttg gagggcacaa aagtgagaag
2281 ccggctctgc ctcggaagag ggcaggggag aacaggtctg accaggtgac ccgaggcaca
2341 gtaacgcctc cccccaggct ggtgaaaaag aatgaggaag ctgctgatga ggtcttcaaa
2401 gacatcatgg agtccagccc gggctccagc ccgcccaacc tgactccaaa acccctccgg
2461 cggcaggtca ccgtggcccc tgcctcgggc ctcccccaca aggaagaagc tggaaagggc
2521 agtgccttag ggaccccctgc tgcagctgag ccagtgaccc ccaccagcaa agcaggctca
2581 ggtgcaccag ggggcaccag caagggcccc gccgaggagt ccagagtgag gaggcacaag
2641 cactcctctg agtcgccagg gagggacaag gggaaattgt ccaggctcaa acctgccccg
2701 ccgccccac  cagcagcctc tgcaggggag gctggaggaa agccctcgca gagcccgagc
2761 caggaggcgg ccggggaggc agtcctgggc gcaaagacaa aagccacgag tctggttgat
2821 gctgtgaaca gtgacgctgc caagcccagc cagccgggag agggcctcaa aaagcccgtg
2881 ctcccggcca ctccaaagcc acagtccgcc aagccgtcgg ggacccccat cagcccagcc
2941 cccgttccct ccacgttgcc atcagcatcc tcggccctgg cagggggacca gccgtcttcc
3001 accgccttca tccctctcat atcaacccga gtgtctcttc ggaaaaccccg ccagcctcca
3061 gagcggatcg ccagcggcgc catcaccaag gcgtggtcc  tggacagcac cgaggcgctg
3121 tgcctcgcca tctctaggaa ctccgagcag atggccagcc acagcgcagt gctggaggcc
3181 ggcaaaaacc tctacacgtt ctgcgtgagc tatgtggatt ccatccagca aatgaggaac
3241 aagtttgcct tccgagaggc catcaacaaa ctggagaata atctccggga gcttcagatc
```

FIG. 1 (cont'd)

```
3301 tgcccggcga cagcaggcag tggtccagcg gccactcagg acttcagcaa gctcctcagt
3361 tcggtgaagg aaatcagtga catagtgcag aggtagcagc agtcaggggt caggtgtcag
3421 gcccgtcgga gctgcctgca gcacatgcgg gctcgcccat acccgtgaca gtggctgaca
3481 agggactagt gagtcagcac cttggcccag gagctctgcg ccaggcagag ctgagggccc
3541 tgtggagtcc agctctacta cctacgtttg caccgcctgc cctcccgcac cttcctcctc
3601 cccgctccgt ctctgtcctc gaattttatc tgtggagttc ctgctccgtg gactgcagtc
3661 ggcatgccag gacccgccag ccccgctccc acctagtgcc ccagactgag ctctccaggc
3721 caggtgggaa cggctgatgt ggactgtctt tttcatttt ttctctctgg agccctcct
3781 cccccggctg ggcctccttc ttccacttct ccaagaatgg aagcctgaac tgaggccttg
3841 tgtgtcaggc cctctgcctg cactccctgg ccttgcccgt cgtgtgctga agacatgttt
3901 caagaaccgc atttcgggaa gggcatgcac gggcatgcac acggctggtc actctgccct
3961 ctgctgctgc ccggggtggg gtgcactcgc catttcctca cgtgcaggac agctcttgat
4021 ttgggtggaa aacagggtgc taaagccaac cagcctttgg gtcctgggca ggtgggagct
4081 gaaaggatc gaggcatggg gcatgtcctt tccatctgtc cacatcccca gagcccagct
4141 cttgctctct tgtgacgtgc actgtgaatc ctggcaagaa agcttgagtc tcaagggtgg
4201 caggtcactg tcactgccga catccctccc ccagcagaat ggaggcaggg gacaagggag
4261 gcagtggcta gtggggtgaa cagctggtgc caaatagccc cagactgggc ccaggcaggt
4321 ctgcaagggc ccagagtgaa ccgtcctttc acacatctgg gtgccctgaa agggcccttc
4381 ccctccccca ctcctctaag acaaagtaga ttcttacaag gcccttcct ttggaacaag
4441 acagccttca cttttctgag ttcttgaagc atttcaaagc cctgcctctg tgtagccgcc
4501 ctgagagaga atagagctgc cactgggcac ctgcgcacag gtgggaggaa agggcctggc
4561 cagtcctggt cctggctgca ctcttgaact gggcgaatgt cttatttaat taccgtgagt
4621 gacatagcct catgttctgt ggggtcatc agggagggtt aggaaaacca caaacggagc
4681 ccctgaaagc ctcacgtatt tcacagagca cgcctgccat cttctccccg aggctgcccc
4741 aggccggagc ccagatacgg gggctgtgac tctgggcagg gacccggggt ctcctggacc
4801 ttgacagagc agctaactcc gagagcagtg ggcaggtggc cgccccctgag gcttcacgcc
4861 gggagaagcc accttcccac cccttcatac cgcctcgtgc cagcagcctc gcacaggccc
4921 tagctttacg ctcatcacct aaacttgtac tttattttc tgatagaaat ggtttcctct
4981 ggatcgtttt atgcggttct tacagcacat cacctctttg ccccgacgg ctgtgacgca
5041 gccggaggga ggcactagtc accgacagcg gccttgaaga cagagcaaag cgcccaccca
5101 ggtcccccga ctgcctgtct ccatgaggta ctggtccctt ccttttgtta acgtgatgtg
5161 ccactatatt ttacacgtat ctcttggtat gcatctttta tagacgctct tttctaagtg
5221 gcgtgtgcat agcgtcctgc cctgccccct cggggcctg tggtggctcc ccctctgctt
5281 ctcggggtcc agtgcatttt gtttctgtat atgattctct gtggtttttt ttgaatccaa
5341 atctgtcctc tgtagtattt tttaaataaa tcagtgttta catt
```

FIG. 2

```
    1  MLEICLKLVG  CKSKKGLSSS  SSCYLEEALQ  RPVASDFEPQ  GLSEAARWNS
   51  KENLLAGPSE  NDPNLFVALY  DFVASGDNTL  SITKGEKLRV  LGYNHNGEWC
  101  EAQTKNGQGW  VPSNYITPVN  SLEKHSWYHG  PVSRNAAEYL  LSSGINGSFL
  151  VRESESSPGQ  RSISLRYEGR  VYHYRINTAS  DGKLYVSSES  RFNTLAELVH
  201  HHSTVADGLI  TTLHYPAPKR  NKPTVYGVSP  NYDKWEMERT  DITMKHKLGG
  251  GQYGEVYEGV  WKKYSLTVAV  KTLKEDTMEV  EEFLKEAAVM  KEIKHPNLVQ
  301  LLGVCTREPP  FYIITEFMTY  GNLLDYLREC  NRQEVNAVVL  LYMATQISSA
  351  MEYLEKKNFI  HRDLAARNCL  VGENHLVKVA  DFGLSRLMTG  DTYTAHAGAK
  401  FPIKWTAPES  LAYNKFSIKS  DVWAFGVLLW  EIATYGMSPY  PGIDLSQVYE
  451  LLEKDYRMER  PEGCPEKVYE  LMRACWQWNP  SDRPSFAEIH  QAFETMFQES
  501  SISDEVEKEL  GKQGVRGAVS  TLLQAPELPT  KTRTSRRAAE  HRDTTDVPEM
  551  PHSKGQGESD  PLDHEPAVSP  LLPRKERGPP  EGGLNEDERL  LPKDKKTNLF
  601  SALIKKKKKT  APTPPKRSSS  FREMDGQPER  RGAGEEEGRD  ISNGALAFTP
  651  LDTADPAKSP  KPSNGAGVPN  GALRESGGSG  FRSPHLWKKS  STLTSSRLAT
  701  GEEEGGGSSS  KRFLRSCSAS  CVPHGAKDTE  WRSVTLPRDL  QSTGRQFDSS
  751  TFGGHKSEKP  ALPRKRAGEN  RSDQVTRGTV  TPPPRLVKKN  EEAADEVFKD
  801  IMESSPGSSP  PNLTPKPLRR  QVTVAPASGL  PHKEEAGKGS  ALGTPAAAEP
  851  VTPTSKAGSG  APGGTSKGPA  EESRVRRHKH  SSESPGRDKG  KLSRLKPAPP
  901  PPPAASAGKA  GGKPSQSPSQ  EAAGEAVLGA  KTKATSLVDA  VNSDAAKPSQ
  951  PGEGLKKPVL  PATPKPQSAK  PSGTPISPAP  VPSTLPSASS  ALAGDQPSST
 1001  AFIPLISTRV  SLRKTRQPPE  RIASGAITKG  VVLDSTEALC  LAISRNSEQM
 1051  ASHSAVLEAG  KNLYTFCVSY  VDSIQQMRNK  FAFREAINKL  ENNLRELQIC
 1101  PATAGSGPAA  TQDFSKLLSS  VKEISDIVQR
```

FIG. 3

```
   1  aaaatgttgg agatctgcct gaagctggtg ggctgcaaat ccaagaaggg
  51  gctgtcctcg tcctccagct gttatctgga agaagcccttt cagcggccag
 101  tagcatctga ctttgagcct cagggtctga gtgaagccgc tcgttggaac
 151  tccaaggaaa accttctcgc tggacccagt gaaaatgacc ccaacctttt
 201  cgttgcactg tatgattttg tggccagtgg agataacact ctaagcataa
 251  ctaaaggtga aaagctccgg gtcttaggct ataatcacaa tggggaatgg
 301  tgtgaagccc aaaccaaaaa tggccaaggc tgggtcccaa gcaactacat
 351  cacgccagtc aacagtctgg agaaacactc ctggtaccat gggcctgtgt
 401  cccgcaatgc cgctgagtat ctgctgagca gcgggatcaa tggcagcttc
 451  ttggtgcgtg agagtgagag cagtcctggc cagaggtcca tctcgctgag
 501  atacgaaggg agggtgtacc attacaggat caacactgct tctgatggca
 551  aggggagctg ctggtgagga ttattttaga ctgtgagtaa ttgacctgac
 601  agacagtgat gactgcttca ttaagagccc acgaccacgt gccagaatag
 651  ttcagcatcc tctgttgcta ctgtactttg agacatcgtt cttctttgtg
 701  atgcaatacc tctttcttgt catgagggtc tcttccctta aatcaggctc
 751  tacgtctcct ccgagagccg cttcaacacc ctggccgagt tggttcatca
 801  tcattcaacg gtggccgacg ggctcatcac cacgctccat tatccagccc
 851  caaagcgcaa caagcccact gtctatggtg tgtcccccaa ctacgacaag
 901  tgggagatgg aacgcacgga catcaccatg aagcacaagc tgggcggggg
 951  ccagtacggg gaggtgtacg agggcgtgtg gaagaaatac agcctgacgg
1001  tggccgtgaa gaccttgaag gaggacacca tggaggtgga agagttcttg
1051  aaagaagctg cagtcatgaa agagatcaaa caccctaacc tggtgcagct
1101  ccttggggtc tgcacccggg agccccgtt ctatatcatc actgagttca
1151  tgacctacgg gaacctcctg gactacctga gggagtgcaa ccggcaggag
1201  gtgaacgccg tggtgctgct gtacatggcc actcagatct cgtcagccat
1251  ggagtacctg gagaagaaaa acttcatcca cagagatctt gctgcccgaa
1301  actgcctggt aggggagaac cacttggtga aggtagctga ttttggcctg
1351  agcaggttga tgacagggga cacctacaca gcccatgctg gagccaagtt
1401  ccccatcaaa tggactgcac ccgagagcct ggcctacaac aagttctcca
1451  tcaagtccga cgtctgggca tttggagtat tgctttggga aattgctacc
1501  tatggcatgt ccccttaccc gggaattgac ctgtcccagg tgtatgagct
1551  gctagagaag gactaccgca tggagcgccc agaaggctgc ccagagaagg
1601  tctatgaact catgcgagca tgttggcagt ggaatccctc tgaccggccc
1651  tcctttgctg aaatccacca agcctttgaa acaatgttcc aggaatccag
1701  tatctcagac gaagtggaaa aggagctggg gaaacaaggc gtccgtgggg
1751  ctgtgagtac cttgctgcag gccccagagc tgcccaccaa gacgaggacc
1801  tccaggagag ctgcagagca cagagacacc actgacgtgc ctgagatgcc
1851  tcactccaag ggccagggag agagcgatcc tctggaccat gagcctgccg
1901  tgtctccatt gctccctcga aaagagcgag gtccccggga gggcggcctg
1951  aatgaagatg agcgccttct ccccaaagac aaaagacca acttgttcag
2001  cgccttgatc aagaagaaga agaagacagc cccaaccccct cccaaacgca
2051  gcagctcctt ccgggagatg gacggccagc cggagcgcag aggggccggc
2101  gaggaagagg gccgagacat cagcaacggg gcactggctt tcaccccctt
2151  ggacacagct gaccagcca agtccccaaa gccagcaat ggggctgggg
2201  tccccaatgg agccctccgg gagtccgggg gctcaggctt ccggtctccc
2251  cacctgtgga agaagtccag cacgctgacc agcagccgcc tagccaccgg
2301  cgaggaggag ggcggtggca gctccagcaa gcgttcctg cgctcttgct
2351  ccgcctcctg cgttccccat ggggccaagg acacggagtg gaggtcagtc
2401  acgctgcctc gggacttgca gtccacggga agacagtttg actcgtccac
2451  atttggaggg cacaaaagtg agaagccggc tctgcctcgg aagagggcag
2501  gggagaacag gtctgaccag gtgacccgag gcacagtaac gcctccccc
2551  aggctggtga aaagaatga ggaagctgct gatgaggtct tcaaagacat
2601  catggagtcc agcccgggct ccagcccgcc caacctgact ccaaaacccc
2651  tccggcggca ggtcaccgtg gcccctgcct cgggcctccc ccacaaggaa
2701  gaagctggaa agggcagtgc cttagggacc cctgctgcag ctgagccagt
```

FIG. 3 (cont'd)

```
2751  gaccccacc  agcaaagcag  gctcaggtgc  accaggggc   accagcaagg
2801  gccccgccga  ggagtccaga  gtgaggaggc  acaagcactc  ctctgagtcg
2851  ccagggaggg  acaaggggaa  attgtccagg  ctcaaacctg  ccccgccgcc
2901  cccaccagca  gcctctgcag  ggaaggctgg  aggaaagccc  tcgcagagcc
2951  cgagccagga  ggcggccggg  gaggcagtcc  tgggcgcaaa  gacaaaagcc
3001  acgagtctgg  ttgatgctgt  gaacagtgac  gctgccaagc  ccagccagcc
3051  gggagagggc  ctcaaaaagc  ccgtgctccc  ggccactcca  aagccacagt
3101  ccgccaagcc  gtcggggacc  cccatcagcc  cagccccgt   tccctccacg
3151  ttgccatcag  catcctcggc  cctggcaggg  gaccagccgt  cttccaccgc
3201  cttcatccct  ctcatatcaa  cccgagtgtc  tcttcggaaa  acccgccagc
3251  ctccagagcg  gatcgccagc  ggcgccatca  ccaagggcgt  ggtcctggac
3301  agcaccgagg  cgctgtgcct  cgccatctct  aggaactccg  agcagatggc
3351  cagccacagc  gcagtgctgg  aggccggcaa  aaacctctac  acgttctgcg
3401  tgagctatgt  ggattccatc  cagcaaatga  ggaacaagtt  tgccttccga
3451  gaggccatca  acaaactgga  gaataatctc  cgggagcttc  agatctgccc
3501  ggcgacagca  ggcagtggtc  cagcggccac  tcaggacttc  agcaagctcc
3551  tcagttcggt  gaaggaaatc  agtgacatag  tgcagaggta  gcagcagtca
3601  ggggtcaggt  gtcaggcccg  tcggagctgc  ctgcagcaca  tgcgggctcg
3651  cccatacccg  tgacagtggc  tgacaaggga  ctagtgagtc  agcaccttgg
3701  cccaggagct  ctgcgccagg  cagagctgag  ggcctgtgg   agtccagctc
3751  tactacctac  gtttgcaccg  cctgccctcc  cgcaccttcc  tcctccccgc
3801  tccgtctctg  tcctcgaatt  ttatctgtgg  agttcctgct  ccgtggactg
3851  cagtcggcat  gccaggaccc  gccagcccg   ctcccaccta  gtgccccaga
3901  ctgagctctc  caggccaggt  gggaacggct  gatgtggact  gtctttttca
3951  ttttttttctc  tctggagccc  ctcctccccc  ggctgggcct  ccttcttcca
4001  cttctccaag  aatggaagcc  tgaactgagg  ccttgtgtgt  caggccctct
4051  gcctgcactc  cctggccttg  cccgtcgtgt  gctgaagaca  tgtttcaaga
4101  accgcatttc  gggaagggca  tgcacgggca  tgcacacggc  tggtcactct
4151  gccctctgct  gctgccgggg  gtggggtgca  ctcgccatt   cctcacgtgc
4201  aggacagctc  ttgatttggg  tggaaaacag  ggtgctaaag  ccaaccagcc
4251  tttgggtcct  gggcaggtgg  gagctgaaaa  ggatcgaggc  atggggcatg
4301  tcctttccat  ctgtccacat  ccccagagcc  cagctcttgc  tctcttgtga
4351  cgtgcactgt  gaatcctggc  aagaaagctt  gagtctcaag  ggtggcaggt
4401  cactgtcact  gccgacatcc  ctcccccagc  agaatggagg  caggggacaa
4451  gggaggcagt  ggctagtggg  gtgaacagct  ggtgccaaat  agccccagac
4501  tgggcccagg  caggtctgca  agggcccaga  gtgaaccgtc  ctttcacaca
4551  tctgggtgcc  ctgaaaggc   ccttcccctc  ccccactcct  ctaagacaaa
4601  gtagattctt  acaaggccct  ttcctttgga  acaagacagc  cttcacttt
4651  ctgagttctt  gaagcatttc  aaagccctgc  ctctgtgtag  ccgccctgag
4701  agagaataga  gctgccactg  ggcacctgcg  cacaggtggg  aggaaagggc
4751  ctggccagtc  ctggtcctgg  ctgcactctt  gaactgggcg  aatgtcttat
4801  ttaattaccg  tgagtgacat  agcctcatgt  tctgtggggg  tcatcaggga
4851  gggttaggaa  aaccacaaac  ggagcccctg  aaagcctcac  gtatttcaca
4901  gagcacgcct  gccatcttct  ccccgaggct  gcccaggcc   ggagcccaga
4951  tacggggct   gtgactctgg  gcagggaccc  ggggtctcct  ggaccttgac
5001  agagcagcta  actccgagag  cagtgggcag  gtggccgccc  ctgaggcttc
5051  acgccgggag  aagccacctt  cccaccctt   catccgcct   cgtgccagca
5101  gcctcgcaca  ggccctagct  ttacgctcat  cacctaaact  tgtactttat
5151  ttttctgata  gaaatggttt  cctctggatc  gttttatgcg  gttcttacag
5201  cacatcacct  ctttgccccc  gacggctgtg  acgcagccgg  agggaggcac
5251  tagtcaccga  cagcggcctt  gaagacagag  caaagcgccc  acccaggtcc
5301  cccgactgcc  tgtctccatg  aggtactggt  cccttccttt  tgttaacgtg
5351  atgtgccact  atattttaca  cgtatctctt  ggtatgcatc  ttttatagac
5401  gctcttttct  aagtggcgtg  tgcatagcgt  cctgccctgc  ccctcgggg
5451  gcctgtggtg  gctccccctc  tgcttctcgg  ggtccagtgc  attttgtttc
```

FIG. 3 (cont'd)

```
5501 tgtatatgat tctctgtggt tttttttgaa tccaaatctg tcctctgtag
5551 tatttttaa ataaatcagt gtttacatt
```

FIG. 4

```
   1  aaaatgttgg agatctgcct gaagctggtg ggctgcaaat ccaagaaggg
  51  gctgtcctcg tcctccagct gttatctgga agaagcccct cagcggccag
 101  tagcatctga ctttgagcct caggtctga gtgaagccgc tcgttggaac
 151  tccaaggaaa accttctcgc tggaccagt gaaaatgacc ccaaccttt
 201  cgttgcactg tatgattttg tggccagtgg agataacact ctaagcataa
 251  ctaaggtga aaagctccgg gtcttaggct ataatcacaa tggggaatgg
 301  tgtgaagccc aaaccaaaaa tggccaagc tgggtccaa gcaactacat
 351  cacgccagtc aacagtctgg agaaacactc ctggtaccat gggcctgtgt
 401  cccgcaatgc cgctgagtat ctgctgagca gcgggatcaa tggcagcttc
 451  ttggtgcgtg agagtgagag cagtcctggc cagaggtcca tctcgctgag
 501  atacgaaggg agggtgtacc attacaggat caacactgct tctgatgca
 551  agctctacgt ctcctccgag agccgcttca acaccctggc cgagttggtt
 601  catcatcatt caacggtggc cgacgggctc atcaccacgc tccattatcc
 651  agccccaaag cgcaacaagc ccactgtcta tggtgtgtcc cccaactacg
 701  acaagtggga gatggaacgc acggacatca ccatgaagca caagctgggc
 751  gggggccagt acgggaggt gtacgagggc gtgtggaaga aatacagcct
 801  gacggtggcc gtgaagacct gaaggagga caccatggag gtggaagagt
 851  tcttgaaaga agctgcagtc atgaaagaga tcaaacaccc taacctggtg
 901  cagctccttg gtaggggcct ggccaggcag cctgcgccat ggagtcacag
 951  ggcgtggagc cgggcagcct tttacaaaaa gccccagcct aggaggtctc
1001  agggcgcagc ttctaacctc agtgctggca acacattgga ccttggaaca
1051  aaggcaaaca ctaggctcct ggcaaagcca gctttgggca tgcatccagg
1101  gctaaattca gccaggccta gactctggac cagtggagca gctaatcccc
1151  ggagggtctg caccccggag cccccgttct atatcatcac tgagttcatg
1201  acctacggga acctcctgga ctacctgagg gagtgcaacc ggcaggaggt
1251  gaacgccgtg gtgctgctgt acatggccac tcagatctcg tcagccatgg
1301  agtacctgga gaagaaaaac ttcatccaca gagatcttgc tgcccgaaac
1351  tgcctggtag gggagaacca cttggtgaag gtagctgatt ttggcctgag
1401  caggttgatg acaggggaca cctacacagc ccatgctgga gccaagttcc
1451  ccatcaaatg gactgcaccc gagagcctgg cctacaacaa gttctccatc
1501  aagtccgacg tctgggcatt tggagtattg ctttgggaaa ttgctaccta
1551  tggcatgtcc ccttacccgg gaattgacct gtcccaggtg tatgagctgc
1601  tagagaagga ctaccgcatg gagcgcccag aaggctgccc agagaaggtc
1651  tatgaactca tgcgagcatg ttggcagtgg aatccctctg accggccctc
1701  ctttgctgaa atccaccaag cctttgaaac aatgttccag gaatccagta
1751  tctcagacga agtggaaaag gagctgggga acaaggcgt ccgtggggct
1801  gtgagtacct tgctgcaggc cccagagctg cccaccaaga cgaggacctc
1851  caggagagct gcagagcaca gagacaccac tgacgtgcct gagatgcctc
1901  actccaaggg ccagggagag agcgatcctc tggaccatga gcctgccgtg
1951  tctccattgc tccctcgaaa agagcgaggt cccccggagg gcggcctgaa
2001  tgaagatgag cgccttctcc ccaaagacaa aaagaccaac ttgttcagcg
2051  ccttgatcaa gaagaagaag aagacagccc caaccctcc caaacgcagc
2101  agctccttcc gggagatgga cggccagccg gagcgcagag gggccggcga
2151  ggaagagggc cgagacatca gcaacgggc actggcttc acccccttgg
2201  acacagctga cccagccaag tccccaaagc ccagcaatgg ggctggggtc
2251  cccaatggag ccctccggga gtccggggc tcaggcttcc ggtctcccca
2301  cctgtggaag aagtccagca cgctgaccag cagccgccta gccaccggcg
2351  aggaggaggg cggtgcagc tccagcaagc gcttcctgcg ctcttgctcc
2401  gcctcctgcg ttccccatgg ggccaaggac acggagtgga ggtcagtcac
2451  gctgcctcgg gacttgcagt ccacgggaag acagtttgac tcgtccacat
2501  ttggagggca caaagtgag aagccggctc tgcctcggaa gagggcaggg
2551  gagaacaggt ctgaccaggt gacccgaggc acagtaacgc ctccccccag
2601  gctggtgaaa aagaatgagg aagctgctga tgaggtcttc aagacatca
2651  tggagtccag cccgggctcc agccgccca acctgactcc aaaaccctc
2701  cggcggcagg tcaccgtggc ccctgcctcg ggcctccccc acaaggaaga
```

FIG. 4 (cont'd)

```
2751   agctggaaag ggcagtgcct tagggacccc tgctgcagct gagccagtga
2801   cccccaccag caaagcaggc tcaggtgcac caggggcac cagcaagggc
2851   cccgccgagg agtccagagt gaggaggcac aagcactcct ctgagtcgcc
2901   agggagggac aagggggaaat tgtccaggct caaacctgcc ccgccgcccc
2951   caccagcagc ctctgcaggg aaggctggag gaaagccctc gcagagcccg
3001   agccaggagg cggccgggga ggcagtcctg ggcgcaaaga caaaagccac
3051   gagtctggtt gatgctgtga acagtgacgc tgccaagccc agccagccgg
3101   gagagggcct caaaaagccc gtgctcccgg ccactccaaa gccacagtcc
3151   gccaagccgt cggggacccc catcagccca gcccccgttc cctccacgtt
3201   gccatcagca tcctcggccc tggcagggga ccagccgtct tccaccgcct
3251   tcatccctct catatcaacc cgagtgtctc ttcggaaaac ccgccagcct
3301   ccagagcgga tcgccagcgg cgccatcacc aagggcgtgg tcctggacag
3351   caccgaggcg ctgtgcctcg ccatctctag gaactccgag cagatgccca
3401   gccacagcgc agtgctggag gccggcaaaa acctctacac gttctgcgtg
3451   agctatgtgg attccatcca gcaaatgagg aacaagtttg ccttccgaga
3501   ggccatcaac aaactggaga ataatctccg ggagcttcag atctgcccgg
3551   cgacagcagg cagtggtcca gcggccactc aggacttcag caagctcctc
3601   agttcggtga aggaaatcag tgacatagtg cagaggtagc agcagtcagg
3651   ggtcaggtgt caggcccgtc ggagctgcct gcagcacatg cgggctcgcc
3701   catacccgtg acagtggctg acaagggact agtgagtcag caccttggcc
3751   caggagctct gcgccaggca gagctgaggg ccctgtggag tccagctcta
3801   ctacctacgt ttgcaccgcc tgccctcccg caccttcctc ctccccgctc
3851   cgtctctgtc ctcgaatttt atctgtggag ttcctgctcc gtggactgca
3901   gtcggcatgc caggacccgc cagccccgct cccacctagt gccccagact
3951   gagctctcca ggccaggtgg gaacggctga tgtggactgt cttttcatt
4001   tttttctctc tggagcccct cctcccccgg ctgggcctcc ttcttccact
4051   tctccaagaa tggaagcctg aactgaggcc ttgtgtgtca ggccctctgc
4101   ctgcactccc tggccttgcc cgtcgtgtgc tgaagacatg tttcaagaac
4151   cgcatttcgg gaagggcatg cacgggcatg cacacggctg gtcactctgc
4201   cctctgctgc tgcccggggt ggggtgcact cgccatttcc tcacgtgcag
4251   gacagctctt gatttgggtg gaaaacaggg tgctaaagcc aaccagcctt
4301   tgggtcctgc gcaggtggga gctgaaaagg atcgaggcat ggggcatgtc
4351   ctttccatct gtccacatcc ccagagccca gctcttgctc tcttgtgacg
4401   tgcactgtga atcctggcaa gaaagcttga gtctcaaggg tggcaggtca
4451   ctgtcactgc cgacatccct cccccagcag aatggaggca ggggacaagg
4501   gaggcagtgg ctagtggggt gaacagctgg tgccaaatag ccccagactg
4551   ggcccaggca ggtctgcaag ggcccagagt gaaccgtcct ttcacacatc
4601   tgggtgccct gaaagggccc ttcccctccc ccactcctct aagacaaagt
4651   agattcttac aaggccctt cctttggaac aagacagcct tcacttttct
4701   gagttcttga agcatttcaa agccctgcct ctgtgtagcc gccctgagag
4751   agaatagagc tgccactggg cacctgcgca caggtgggag gaaagggcct
4801   ggccagtcct ggtcctggct gcactcttga actgggcgaa tgtcttattt
4851   aattaccgtg agtgacatag cctcatgttc tgtggggtc atcagggagg
4901   gttaggaaaa ccacaaacgg agccctgaa agcctcacgt atttcacaga
4951   gcacgcctgc catcttctcc ccgaggctgc cccaggccgg agcccagata
5001   cggggctgt gactctgggc agggacccgg ggtctcctgg accttgacag
5051   agcagctaac tccgagagca gtgggcaggt ggccgcccct gaggcttcac
5101   gccggagaa gccaccttcc cacccettca taccgcctcg tgccagcagc
5151   ctcgcacagg ccctagcttt acgctcatca cctaaacttg tactttattt
5201   ttctgataga aatggtttcc tctggatcgt tttatgcggt tcttacagca
5251   catcacctct ttgccccga cggctgtgac gcagccggag ggaggcacta
5301   gtcaccgaca gcggccttga agacagagca aagcgcccac ccaggtcccc
5351   cgactgcctg tctccatgag gtactggtcc cttccttttg ttaacgtgat
5401   gtgccactat attttacacg tatctcttgg tatgcatctt ttatagacgc
5451   tcttttctaa gtggcgtgtg catagcgtcc tgccctgccc cctcggggc
```

FIG. 4 (cont'd)

```
5501 ctgtggtggc tccccctctg cttctcgggg tccagtgcat tttgtttctg
5551 tatatgattc tctgtggttt tttttgaatc caaatctgtc ctctgtagta
5601 tttttttaaat aaatcagtgt ttacatt
```

FIG. 5A

```
  1  MLEICLKLVG  CKSKKGLSSS  SSCYLEEALQ  RPVASDFEPQ  GLSEAARWNS
 51  KENLLAGPSE  NDPNLFVALY  DFVASGDNTL  SITKGEKLRV  LGYNHNGEWC
101  EAQTKNGQGW  VPSNYITPVN  SLEKHSWYHG  PVSRNAAEYL  LSSGINGSFL
151  VRESESSPGQ  RSISLRYEGR  VYHYRINTAS  DGKGSCW
```

FIG. 5B

```
   1  MLEICLKLVG  CKSKKGLSSS  SSCYLEEALQ  RPVASDFEPQ  GLSEAARWNS
  51  KENLLAGPSE  NDPNLFVALY  DFVASGDNTL  SITKGEKLRV  LGYNHNGEWC
 101  EAQTKNGQGW  VPSNYITPVN  SLEKHSWYHG  PVSRNAAEYL  LSSGINGSFL
 151  VRESESSPGQ  RSISLRYEGR  VYHYRINTAS  DGKLYVSSES  RFNTLAELVH
 201  HHSTVADGLI  TTLHYPAPKR  NKPTVYGVSP  NYDKWEMERT  DITMKHKLGG
 251  GQYGEVYEGV  WKKYSLTVAV  KTLKEDTMEV  EEFLKEAAVM  KEIKHPNLVQ
 301  LLGRGLARQP  APWSHRAWSR  AAFYKKPQPR  RSQGAASNLS  AGNTLDLGTK
 351  ANTRLLAKPA  LGMHPGLNSA  RPRLWTSGAA  NPRRVCTREP  PFYIITEFMT
 401  YGNLLDYLRE  CNRQEVNAVV  LLYMATQISS  AMEYLEKKNF  IHRDLAARNC
 451  LVGENHLVKV  ADFGLSRLMT  GDTYTAHAGA  KFPIKWTAPE  SLAYNKFSIK
 501  SDVWAFGVLL  WEIATYGMSP  YPGIDLSQVY  ELLEKDYRME  RPEGCPEKVY
 551  ELMRACWQWN  PSDRPSFAEI  HQAFETMFQE  SSISDEVEKE  LGKQGVRGAV
 601  STLLQAPELP  TKTRTSRRAA  EHRDTTDVPE  MPHSKGQGES  DPLDHEPAVS
 651  PLLPRKERGP  PEGGLNEDER  LLPKDKKTNL  FSALIKKKKK  TAPTPPKRSS
 701  SFREMDGQPE  RRGAGEEEGR  DISNGALAFT  PLDTADPAKS  PKPSNGAGVP
 751  NGALRESGGS  GFRSPHLWKK  SSTLTSSRLA  TGEEEGGGSS  SKRFLRSCSA
 801  SCVPHGAKDT  EWRSVTLPRD  LQSTGRQFDS  STFGGHKSEK  PALPRKRAGE
 851  NRSDQVTRGT  VTPPPRLVKK  NEEAADEVFK  DIMESSPGSS  PPNLTPKPLR
 901  RQVTVAPASG  LPHKEEAGKG  SALGTPAAAE  PVTPTSKAGS  GAPGGTSKGP
 951  AEESRVRRHK  HSSESPGRDK  GKLSRLKPAP  PPPPAASAGK  AGGKPSQSPS
1001  QEAAGEAVLG  AKTKATSLVD  AVNSDAAKPS  QPGEGLKKPV  LPATPKPQSA
1051  KPSGTPISPA  PVPSTLPSAS  SALAGDQPSS  TAFIPLISTR  VSLRKTRQPP
1101  ERIASGAITK  GVVLDSTEAL  CLAISRNSEQ  MASHSAVLEA  GKNLYTFCVS
1151  YVDSIQQMRN  KFAFREAINK  LENNLRELQI  CPATAGSGPA  ATQDFSKLLS
1201  SVKEISDIVQ  R
```

FIG. 6

| Amino Acid Sequence of Wild-type BCR-ABL | Amino Acid Sequence of the Kinase Domain Mutant of BCR-ABL | % of Patients Having the Mutation |
|---|---|---|
| M 237 | M 237 I | <2% |
| M 244 | M 244 V | 2-10% |
| L 248 | L 248 V | <2% |
| G 250 | G 250 A | <2% |
| G 250 | G 250 E | 2-10% |
| Q 252 | Q 252 R | <2% |
| Q 252 | Q 252 E | <2% |
| Q 252 | Q 252 H | > 10% |
| Y 253 | Y 253 F | 2-10% |
| Y 253 | Y 253 H | 2-10% |
| E 255 | E 255 V | 2-10% |
| E 255 | E 255 K | > 10% |
| D 276 | D 276 G | <2% |
| V 289 | V 289 I | <2% |
| V 304 | V 304 G | <2% |
| F 311 | F 311 I | <2% |
| F 311 | F 311 L | <2% |
| T 315 | T 315 N | <2% |
| T 315 | T 315 I | > 10% |
| F 317 | F 317 L | 2-10% |
| G 321 | G 321 E | <2% |
| M 343 | M 343 T | <2% |
| M 351 | M 351 T | > 10% |
| E 352 | E 352 G | <2% |
| Y 353 | Y 353 H | <2% |
| E 355 | E 355 D | <2% |
| E 355 | E 355 G | 2-10% |
| F 359 | F 359 A | <2% |
| F 359 | F 359 C | <2% |
| F 359 | F 359 V | 2-10% |
| V 371 | V 371 A | <2% |
| E 373 | E 373 G | <2% |
| V 379 | V 379 I | <2% |
| F 382 | F 382 L | <2% |
| L 387 | L 387 M | <2% |
| T 389 | T 389 A | <2% |
| H 396 | H 396 P | <2% |
| H 396 | H 396 R | 2-10% |
| S 417 | S 417 Y | <2% |
| E 459 | E 459 K | <2% |
| F 486 | F 486 S | <2% |

SEQUENCE LISTING

```
<160> NUMBER OF SEQ ID NOS: 19

<210> SEQ ID NO 1
<211> LENGTH: 5384
<212> TYPE: DNA
<213> ORGANISM: Homo sapiens

<400> SEQUENCE: 1
aaaatgttgg agatctgcct gaagctggtg ggctgcaaat ccaagaaggg gctgtcctcg      60
tcctccagct gttatctgga agaagcccctt cagcggccag tagcatctga ctttgagcct    120
cagggtctga gtgaagccgc tcgttggaac tccaaggaaa accttctcgc tggacccagt    180
gaaaatgacc ccaaccttt cgttgcactg tatgattttg tggccagtgg agataacact     240
ctaagcataa ctaaaggtga aaagctccgg gtcttaggct ataatcacaa tggggaatgg    300
tgtgaagccc aaaccaaaaa tggccaaggc tgggtcccaa gcaactacat cacgccagtc    360
aacagtctgg agaaacactc ctggtaccat gggcctgtgt cccgcaatgc cgctgagtat    420
ctgctgagca gcgggatcaa tggcagcttc ttggtgcgtg agagtgagag cagtcctggc    480
cagaggtcca tctcgctgag atacgaaggg agggtgtacc attacaggat caacactgct    540
tctgatggca agctctacgt ctcctccgag agccgcttca cacccctggc cgagttggtt    600
catcatcatt caacggtggc cgacgggctc atcaccacgc tccattatcc agccccaaag    660
cgcaacaagc ccactgtcta tggtgtgtcc cccaactacg acaagtggga gatggaacgc    720
acggacatca ccatgaagca caagctgggc ggggccagt acggggaggt gtacgagggc    780
gtgtggaaga aatacagcct gacggtggcc gtgaagacct tgaaggagga caccatggag    840
gtggaagagt tcttgaaaga agctgcagtc atgaaagaga tcaaacaccc taacctggtg    900
cagctccttg gggtctgcac ccgggagccc ccgttctata tcatcactga gttcatgacc    960
tacgggaacc tcctggacta cctgagggag tgcaaccggc aggaggtgaa cgccgtggtg   1020
ctgctgtaca tggccactca gatctcgtca gccatggagt acctggagaa gaaaaacttc   1080
atccacagag atcttgctgc ccgaaactgc ctggtagggg agaaccactt ggtgaaggta   1140
gctgattttg gcctgagcag gttgatgaca ggggacacct acacagccca tgctggagcc   1200 aagttccccca tcaaatggac tgcacccgag agcctggcct acaacaagtt ctccatcaag   1260
tccgacgtct gggcatttgg agtattgctt tgggaaattg ctacctatgg catgtcccct   1320
tacccgggaa ttgacctgtc ccaggtgtat gagctgctag agaaggacta ccgcatggag   1380
cgcccagaag gctgcccaga gaaggtctat gaactcatgc gagcatgttg gcagtggaat   1440
ccctctgacc ggccctcctt tgctgaaatc caccaagcct ttgaaacaat gttccaggaa   1500
tccagtatct cagacgaagt ggaaaaggag ctggggaaac aaggcgtccg tgggctgtg   1560 agtaccttgc tgcaggcccc agagctgccc accaagacga ggacctccag gagagctgca   1620
gagcacagag acaccactga cgtgcctgag atgcctcact ccaagggcca gggagagagc   1680
gatccctctg accatgagcc tgccgtgtct ccattgctcc ctcgaaaaga gcgaggtccc   1740
ccggagggcg gcctgaatga agatgagcgc cttctcccca aagacaaaaa gaccaacttg   1800
```

```
ttcagcgcct tgatcaagaa gaagaagaag acagccccaa cccctcccaa acgcagcagc    1860
tccttccggg agatggacgg ccagccgag cgcagagggg ccggcgagga agagggccga    1920
gacatcagca acgggcact ggctttcacc cccttggaca cagctgaccc agccaagtcc     1980
ccaaagccca gcaatggggc tggggtcccc aatggagccc tccgggagtc cgggggctca    2040
ggcttccggt ctccccacct gtggaagaag tccagcacgc tgaccagcag ccgcctagcc    2100
accggcgagg aggagggcgg tggcagctcc agcaagcgct tcctgcgctc ttgctccgcc    2160
tcctgcgttc cccatggggc caaggacacg gagtggaggt cagtcacgct gcctcgggac    2220
ttgcagtcca cggaagaca gtttgactcg tccacatttg gagggcacaa aagtgagaag    2280
ccggctctgc ctcggaagag ggcaggggag aacaggtctg accaggtgac ccgaggcaca    2340
gtaacgcctc cccccaggct ggtgaaaaag aatgaggaag ctgctgatga ggtcttcaaa    2400
gacatcatgg agtccagccc gggctccagc ccgcccaacc tgactccaaa accctccgg    2460 cggcaggtca ccgtggcccc tgcctcgggc ctccccacac aggaagaagc tggaaagggc    2520
agtgccttag ggacccctgc tgcagctgag ccagtgaccc ccaccagcaa agcaggctca    2580
ggtgcaccag ggggcaccag caagggcccc gccgaggagt ccagagtgag gaggcacaag    2640
cactcctctg agtcgccagg gagggacaag gggaaattgt ccaggctcaa acctgccccg    2700
ccgcccccac cagcagcctc tgcagggaag gctggaggaa agccctcgca gagcccgagc    2760
caggaggcgg ccggggaggc agtcctgggc gcaaagacaa aagccacgag tctggttgat    2820
gctgtgaaca gtgacgctgc caagcccagc cagccgggag agggcctcaa aaagcccgtg    2880
ctcccggcca ctccaaagcc acagtccgcc aagccgtcgg ggacccccat cagcccagcc    2940
cccgttccct ccacgttgcc atcagcatcc tcggccctgg caggggacca gccgtcttcc    3000
accgccttca tccctctcat atcaacccga gtgtctcttc ggaaaacccg ccagcctcca    3060
gagcggatcg ccagcggcgc catcaccaag ggcgtggtcc tggacagcac cgaggcgctg    3120
tgcctcgcca tctctaggaa ctccgagcag atggccagcc acagcgcagt gctggaggcc    3180
ggcaaaaacc tctacacgtt ctgcgtgagc tatgtggatt ccatccagca aatgaggaac    3240
aagtttgcct tccgagaggc catcaacaaa ctggagaata atctccggga gcttcagatc    3300
tgcccggcga cagcaggcag tggtccagcg gccactcagg acttcagcaa gctcctcagt    3360
tcggtgaagg aaatcagtga catagtgcag aggtagcagc agtcaggggt caggtgtcag    3420
gcccgtcgga gctgcctgca gcacatgcgg gctcgcccat acccgtgaca gtggctgaca    3480
agggactagt gagtcagcac cttggcccag gagctctgcg ccaggcagag ctgagggccc    3540
tgtggagtcc agctctacta cctacgtttg caccgcctgc cctccgcac cttcctcctc    3600 cccgctccgt ctctgtcctc gaattttatc tgtggagttc ctgctccgtg gactgcagtc    3660
ggcatgccag acccgccag ccccgctccc acctagtgcc ccagactgag ctctccaggc    3720
caggtgggaa cggctgatgt ggactgtctt tttcattttt ttctctctgg agccctcct    3780 cccccggctg ggcctccttc ttccacttct ccaagaatgg aagcctgaac tgaggccttg    3840
tgtgtcaggc cctctgcctg cactcccgg ccttgcccgt cgtgtgctga agacatgttt    3900
caagaaccgc atttcgggaa gggcatgcac gggcatgcac acggctggtc actctgccct    3960
ctgctgctgc ccggggtggg gtgcactcgc catttcctca cgtgcaggac agctcttgat    4020
ttgggtggaa acagggtgc taaagccaac cagcctttgg gtcctgggca ggtgggagct    4080
gaaaaggatc gaggcatggg gcatgtcctt tccatctgtc cacatcccca gagcccagct    4140
```

```
cttgctctct tgtgacgtgc actgtgaatc ctggcaagaa agcttgagtc tcaagggtgg    4200
caggtcactg tcactgccga catccctccc ccagcagaat ggaggcaggg gacaagggag    4260
gcagtggcta gtggggtgaa cagctggtgc aaatagccc cagactgggc ccaggcaggt    4320
ctgcaagggc ccagagtgaa ccgtcctttc acacatctgg gtgccctgaa agggcccttc    4380
ccctccccca ctcctctaag acaaagtaga ttcttacaag gccctttcct ttggaacaag    4440
acagccttca cttttctgag ttcttgaagc atttcaaagc cctgcctctg tgtagccgcc    4500
ctgagagaga atagagctgc cactgggcac ctgcgcacag gtgggaggaa agggcctggc    4560
cagtcctggt cctggctgca ctcttgaact gggcgaatgt cttatttaat taccgtgagt    4620
gacatagcct catgttctgt gggggtcatc agggagggtt aggaaaacca caaacggagc    4680
ccctgaaagc ctcacgtatt tcacagagca cgcctgccat cttctccccg aggctgcccc    4740
aggccggagc ccagatacgg gggctgtgac tctgggcagg gacccggggt ctcctggacc    4800
ttgacagagc agctaactcc gagagcagtg ggcaggtggc cgcccctgag gcttcacgcc    4860
gggagaagcc accttcccac cccttcatac cgcctcgtgc cagcagcctc gcacaggccc    4920
tagctttacg ctcatcacct aaacttgtac tttatttttc tgatagaaat ggtttcctct    4980
ggatcgtttt atgcggttct tacagcacat cacctctttg cccccgacgg ctgtgacgca    5040
gccggaggga ggcactagtc accgacagcg gccttgaaga cagagcaaag cgcccaccca    5100 ggtccccga ctgcctgtct ccatgaggta ctggtcccttccttttgtta acgtgatgtg    5160 ccactatatt ttacacgtat ctcttggtat gcatctttta tagacgctct tttctaagtg    5220
gcgtgtgcat agcgtcctgc cctgccccct cgggggcctg tggtggctcc ccctctgctt    5280
ctcggggtcc agtgcatttt gtttctgtat atgattctct gtggtttttt ttgaatccaa    5340
atctgtcctc tgtagtattt tttaaataaa tcagtgttta catt                    5384
```

<210> SEQ ID NO 2
<211> LENGTH: 1130
<212> TYPE: PRT
<213> ORGANISM: Homo sapiens

<400> SEQUENCE: 2

```
Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160
```

-continued

```
Arg Ser Ile Ser Leu Arg Tyr Glu Gly Arg Val Tyr His Tyr Arg Ile
            165                 170                 175

Asn Thr Ala Ser Asp Gly Lys Leu Tyr Val Ser Ser Glu Ser Arg Phe
        180                 185                 190

Asn Thr Leu Ala Glu Leu Val His His Ser Thr Val Ala Asp Gly
    195                 200                 205

Leu Ile Thr Thr Leu His Tyr Pro Ala Pro Lys Arg Asn Lys Pro Thr
    210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gln Tyr Gly Glu Val
            245                 250                 255

Tyr Glu Gly Val Trp Lys Lys Tyr Ser Leu Thr Val Ala Val Lys Thr
            260                 265                 270

Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Val
        290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
            340                 345                 350

Tyr Leu Glu Lys Lys Asn Phe Ile His Arg Asp Leu Ala Ala Arg Asn
        355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
            405                 410                 415

Ser Ile Lys Ser Asp Val Trp Ala Phe Gly Val Leu Leu Trp Glu Ile
            420                 425                 430

Ala Thr Tyr Gly Met Ser Pro Tyr Pro Gly Ile Asp Leu Ser Gln Val
        435                 440                 445

Tyr Glu Leu Leu Glu Lys Asp Tyr Arg Met Glu Arg Pro Glu Gly Cys
450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495

Phe Gln Glu Ser Ser Ile Ser Asp Glu Val Glu Lys Glu Leu Gly Lys
            500                 505                 510

Gln Gly Val Arg Gly Ala Val Ser Thr Leu Leu Gln Ala Pro Glu Leu
        515                 520                 525

Pro Thr Lys Thr Arg Thr Ser Arg Arg Ala Ala Glu His Arg Asp Thr
530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575
```

```
Arg Gly Pro Pro Glu Gly Gly Leu Asn Glu Asp Glu Arg Leu Leu Pro
            580                 585                 590

Lys Asp Lys Lys Thr Asn Leu Phe Ser Ala Leu Ile Lys Lys Lys Lys
            595                 600                 605

Lys Thr Ala Pro Thr Pro Pro Lys Arg Ser Ser Ser Phe Arg Glu Met
            610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
            660                 665                 670

Leu Arg Glu Ser Gly Gly Ser Gly Phe Arg Ser Pro His Leu Trp Lys
            675                 680                 685

Lys Ser Ser Thr Leu Thr Ser Ser Arg Leu Ala Thr Gly Glu Glu Glu
            690                 695                 700

Gly Gly Gly Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
            755                 760                 765

Glu Asn Arg Ser Asp Gln Val Thr Arg Gly Thr Val Thr Pro Pro Pro
            770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
            820                 825                 830

Lys Glu Glu Ala Gly Lys Gly Ser Ala Leu Gly Thr Pro Ala Ala Ala
            835                 840                 845

Glu Pro Val Thr Pro Thr Ser Lys Ala Gly Ser Gly Ala Pro Gly Gly
            850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
            885                 890                 895

Pro Ala Pro Pro Pro Pro Ala Ala Ser Ala Gly Lys Ala Gly Gly
                900                 905                 910

Lys Pro Ser Gln Ser Pro Ser Gln Glu Ala Ala Gly Glu Ala Val Leu
            915                 920                 925

Gly Ala Lys Thr Lys Ala Thr Ser Leu Val Asp Ala Val Asn Ser Asp
            930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
                965                 970                 975

Ser Pro Ala Pro Val Pro Ser Thr Leu Pro Ser Ala Ser Ser Ala Leu
            980                 985                 990

Ala Gly Asp Gln Pro Ser Ser Thr  Ala Phe Ile Pro Leu  Ile Ser Thr
```

Arg Val Ser Leu Arg Lys Thr Arg Gln Pro Pro Glu Arg Ile Ala
    1010            1015            1020

Ser Gly Ala Ile Thr Lys Gly Val Val Leu Asp Ser Thr Glu Ala
    1025            1030            1035

Leu Cys Leu Ala Ile Ser Arg Asn Ser Glu Gln Met Ala Ser His
    1040            1045            1050

Ser Ala Val Leu Glu Ala Gly Lys Asn Leu Tyr Thr Phe Cys Val
    1055            1060            1065

Ser Tyr Val Asp Ser Ile Gln Gln Met Arg Asn Lys Phe Ala Phe
    1070            1075            1080

Arg Glu Ala Ile Asn Lys Leu Glu Asn Asn Leu Arg Glu Leu Gln
    1085            1090            1095

Ile Cys Pro Ala Thr Ala Gly Ser Gly Pro Ala Ala Thr Gln Asp
    1100            1105            1110

Phe Ser Lys Leu Leu Ser Ser Val Lys Glu Ile Ser Asp Ile Val
    1115            1120            1125

Gln Arg
    1130

<210> SEQ ID NO 3
<211> LENGTH: 5579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
aaaatgttgg agatctgcct gaagctggtg ggctgcaaat ccaagaaggg gctgtcctcg      60
tcctccagct gttatctgga agaagcccct cagcggccag tagcatctga ctttgagcct     120
cagggtctga gtgaagccgc tcgttggaac tccaaggaaa accttctcgc tggacccagt     180
gaaaatgacc ccaaccttt cgttgcactg tatgattttg tggccagtgg agataacact      240
ctaagcataa ctaaaggtga aaagctccgg gtcttaggct ataatcacaa tggggaatgg     300
tgtgaagccc aaaccaaaaa tggccaaggc tgggtcccaa gcaactacat cacgccagtc     360
aacagtctgg agaaacactc ctggtaccat gggcctgtgt cccgcaatgc cgctgagtat     420
ctgctgagca gcgggatcaa tgcagcttc ttggtgcgtg agagtgagag cagtcctggc     480
cagaggtcca tctcgctgag atacgaaggg agggtgtacc attacaggat caacactgct     540
tctgatggca aggggagctg ctggtgagga ttattttaga ctgtgagtaa ttgacctgac     600
agacagtgat gactgcttca ttaagagccc acgaccacgt gccagaatag ttcagcatcc     660
tctgttgcta ctgtactttg agacatcgtt cttctttgtg atgcaatacc tctttcttgt     720
catgagggtc tcttccctta aatcaggctc tacgtctcct ccgagagccg cttcaacacc     780 ctggccagt tggttcatca tcattcaacg gtggccgacg ggctcatcac cacgctccat      840
tatccagccc caaagcgcaa caagcccact gtctatggtg tgtcccccaa ctacgacaag     900
tgggagatgg aacgcacgga catcaccatg aagcacaagc tgggcggggg ccagtacggg     960
gaggtgtacg agggcgtgtg gaagaaatac agcctgacgg tggccgtgaa gaccttgaag    1020
gaggacacca tggaggtgga agagttcttg aaagaagctg cagtcatgaa agagatcaaa    1080
caccctaacc tggtgcagct ccttggggtc tgcacccggg agccccgtt ctatatcatc     1140 actgagttca tgaccaacgg gaacctcctg gactacctga gggagtgcaa ccggcaggag    1200

```
gtgaacgccg tggtgctgct gtacatggcc actcagatct cgtcagccat ggagtacctg    1260
gagaagaaaa acttcatcca cagagatctt gctgcccgaa actgcctggt agggagaac    1320 cacttggtga aggtagctga ttttggcctg agcaggttga tgacagggga cacctacaca    1380
gcccatgctg gagccaagtt ccccatcaaa tggactgcac ccgagagcct ggcctacaac    1440
aagttctcca tcaagtccga cgtctgggca tttggagtat tgctttggga aattgctacc    1500
tatggcatgt ccccttaccc gggaattgac ctgtcccagg tgtatgagct gctagagaag    1560
gactaccgca tggagcgccc agaaggctgc ccagagaagg tctatgaact catgcgagca    1620
tgttggcagt ggaatccctc tgaccggccc tcctttgctg aaatccacca agcctttgaa    1680
acaatgttcc aggaatccag tatctcagac gaagtggaaa aggagctggg gaaacaaggc    1740
gtccgtgggg ctgtgagtac cttgctgcag gccccagagc tgcccaccaa gacgaggacc    1800
tccaggagag ctgcagagca cagagacacc actgacgtgc ctgagatgcc tcactccaag    1860
ggccagggag agagcgatcc tctggaccat gagcctgccg tgtctccatt gctccctcga    1920
aaagagcgag gtcccccgga gggcggcctg aatgaagatg agcgccttct ccccaaagac    1980
aaaaagacca acttgttcag cgccttgatc aagaagaaga agaagacagc cccaaccccct   2040 cccaaacgca gcagctcctt ccgggagatg gacggccagc cggagcgcag aggggccggc    2100
gaggaagagg gccgagacat cagcaacggg gcactggctt tcacccccctt ggacacagct   2160 gacccagcca agtccccaaa gcccagcaat ggggctgggg tccccaatgg agccctccgg    2220
gagtccgggg gctcaggctt ccggtctccc cacctgtgga agaagtccag cacgctgacc    2280
agcagccgcc tagccaccgg cgaggaggag ggcggtggca gctccagcaa gcgcttcctg    2340
cgctcttgct ccgcctcctg cgttccccat ggggccaagg acacggagtg gaggtcagtc    2400
acgctgcctc gggacttgca gtccacggga agacagtttg actcgtccac atttggaggg    2460
cacaaaagtg agaagccggc tctgcctcgg aagagggcag gggagaacag gtctgaccag    2520
gtgacccgag gcacagtaac gcctcccccc aggctggtga aaaagaatga ggaagctgct    2580
gatgaggtct tcaaagacat catggagtcc agcccgggct ccagcccgcc caacctgact    2640
ccaaaacccc tccggcggca ggtcaccgtg gcccctgcct cgggcctccc ccacaaggaa    2700
gaagctggaa agggcagtgc cttagggacc cctgctgcag ctgagccagt gaccccccacc   2760 agcaaagcag gctcaggtgc accaggggggc accagcaagg gccccgccga ggagtccaga   2820
gtgaggaggc acaagcactc ctctgagtcg ccagggaggg acaaggggaa attgtccagg    2880
ctcaaacctg ccccgccgcc cccaccagca gcctctgcag gaaggctgg aggaaagccc    2940 tcgcagagcc cgagccagga ggcggccggg gaggcagtcc tgggcgcaaa gacaaaagcc    3000
acgagtctgt tgatgctgt gaacagtgac gctgccaagc ccagccagcc gggagagggc    3060
ctcaaaaagc ccgtgctccc ggccactcca aagccacagt ccgccaagcc gtcgggggacc   3120 cccatcagcc cagccccgt tccctccacg ttgccatcag catcctcggc cctggcaggg    3180
gaccagccgt cttccaccgc cttcatccct ctcatatcaa cccgagtgtc tcttcggaaa    3240 accccgccagc ctccagagcg gatcgccagc ggcgccatca ccaagggcgt ggtcctggac    3300
agcaccgagg cgctgtgcct cgccatctct aggaactccg agcagatggc cagccacagc    3360
gcagtgctgg aggccggcaa aaacctctac acgttctgcg tgagctatgt ggattccatc    3420
cagcaaatga ggaacaagtt tgccttccga gaggccatca caaaactgga gaataatctc    3480
cgggagcttc agatctgccc ggcgacagca ggcagtggtc cagcggccac tcaggacttc    3540
```

| | | | | |
|---|---|---|---|---|
| agcaagctcc | tcagttcggt | gaaggaaatc | agtgacatag | tgcagaggta gcagcagtca | 3600 |
| ggggtcaggt | gtcaggcccg | tcggagctgc | ctgcagcaca | tgcgggctcg cccatacccg | 3660 |
| tgacagtggc | tgacaaggga | ctagtgagtc | agcaccttgg | cccaggagct ctgcgccagg | 3720 |
| cagagctgag | ggccctgtgg | agtccagctc | tactacctac | gtttgcaccg cctgccctcc | 3780 |
| cgcaccttcc | tcctccccgc | tccgtctctg | tcctcgaatt | ttatctgtgg agttcctgct | 3840 |
| ccgtggactg | cagtcggcat | gccaggaccc | gccagcccg | ctcccaccta gtgcccaga | 3900 |
| ctgagctctc | caggccaggt | gggaacggct | gatgtggact | gtcttttttca ttttttttctc | 3960 |
| tctggagccc | ctcctccccc | ggctgggcct | ccttcttcca | cttctccaag aatggaagcc | 4020 |
| tgaactgagg | ccttgtgtgt | caggccctct | gcctgcactc | cctggccttg cccgtcgtgt | 4080 |
| gctgaagaca | tgtttcaaga | accgcatttc | gggaagggca | tgcacgggca tgcacacggc | 4140 |
| tggtcactct | gccctctgct | gctgcccggg | gtggggtgca | ctcgccattt cctcacgtgc | 4200 |
| aggacagctc | ttgatttggg | tggaaaacag | ggtgctaaag | ccaaccagcc tttgggtcct | 4260 |
| gggcaggtgg | gagctgaaaa | ggatcgaggc | atggggcatg | tcctttccat ctgtccacat | 4320 |
| ccccagagcc | cagctcttgc | tctcttgtga | cgtgcactgt | gaatcctggc aagaaagctt | 4380 |
| gagtctcaag | ggtggcaggt | cactgtcact | gccgacatcc | ctcccccagc agaatggagg | 4440 |
| caggggacaa | gggaggcagt | ggctagtggg | gtgaacagct | ggtgccaaat agccccagac | 4500 |
| tgggcccagg | caggtctgca | agggcccaga | gtgaaccgtc | ctttcacaca tctgggtgcc | 4560 |
| ctgaaagggc | ccttcccctc | ccccactcct | ctaagacaaa | gtagattctt acaaggccct | 4620 |
| ttcctttgga | acaagacagc | cttcactttt | ctgagttctt | gaagcatttc aaagccctgc | 4680 |
| ctctgtgtag | ccgccctgag | agagaataga | gctgccactg | ggcacctgcg cacaggtggg | 4740 |
| aggaaagggc | ctggccagtc | ctggtcctgg | ctgcactctt | gaactgggcg aatgtcttat | 4800 |
| ttaattaccg | tgagtgacat | agcctcatgt | tctgtggggg | tcatcaggga gggttaggaa | 4860 |
| aaccacaaac | ggagccctg | aaagcctcac | gtatttcaca | gagcacgcct gccatcttct | 4920 |
| ccccgaggct | gccccaggcc | ggagcccaga | tacgggggct | gtgactctgg gcagggaccc | 4980 |
| ggggtctcct | ggaccttgac | agagcagcta | actccgagag | cagtgggcag gtggccgccc | 5040 |
| ctgaggcttc | acgccgggag | aagccacctt | cccaccccctt | cataccgcct cgtgccagca | 5100 |
| gcctcgcaca | ggccctagct | ttacgctcat | cacctaaact | tgtactttat ttttctgata | 5160 |
| gaaatggttt | cctctggatc | gttttatgcg | gttcttacag | cacatcacct ctttgccccc | 5220 |
| gacggctgtg | acgcagccgg | agggaggcac | tagtcaccga | cagcggcctt gaagacagag | 5280 |
| caaagcgccc | acccaggtcc | cccgactgcc | tgtctccatg | aggtactggt cccttccttt | 5340 |
| tgttaacgtg | atgtgccact | atattttaca | cgtatctctt | ggtatgcatc ttttatagac | 5400 |
| gctcttttct | aagtggcgtg | tgcatagcgt | cctgccctgc | cccctcgggg gcctgtggtg | 5460 |
| gctcccccctc | tgcttctcgg | ggtccagtgc | attttgtttc | tgtatatgat tctctgtggt | 5520 |
| ttttttttgaa | tccaaatctg | tcctctgtag | tattttttaa | ataaatcagt gtttacatt | 5579 |

<210> SEQ ID NO 4
<211> LENGTH: 5627
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4

-continued

```
aaaatgttgg agatctgcct gaagctggtg ggctgcaaat ccaagaaggg gctgtcctcg      60
tcctccagct gttatctgga agaagcccct cagcggccag tagcatctga ctttgagcct    120
cagggtctga gtgaagccgc tcgttggaac tccaaggaaa accttctcgc tggacccagt    180
gaaaatgacc ccaaccttt cgttgcactg tatgattttg tggccagtgg agataacact     240
ctaagcataa ctaaaggtga aaagctccgg gtcttaggct ataatcacaa tggggaatgg    300
tgtgaagccc aaaccaaaaa tggccaaggc tgggtcccaa gcaactacat cacgccagtc    360
aacagtctgg agaaacactc ctggtaccat gggcctgtgt cccgcaatgc cgctgagtat    420
ctgctgagca gcgggatcaa tggcagcttc ttggtgcgtg agagtgagag cagtcctggc    480
cagaggtcca tctcgctgag atacgaaggg agggtgtacc attacaggat caacactgct    540
tctgatggca agctctacgt ctcctccgag agccgcttca acaccctggc cgagttggtt    600
catcatcatt caacggtggc cgacgggctc atcaccacgc tccattatcc agccccaaag    660
cgcaacaagc ccactgtcta tggtgtgtcc cccaactacg acaagtggga gatggaacgc    720
acggacatca ccatgaagca caagctgggc gggggccagt acggggaggt gtacgagggc    780
gtgtggaaga atacagcct gacggtggcc gtgaagacct tgaaggagga caccatggag     840
gtggaagagt tcttgaaaga agctgcagtc atgaaagaga tcaaacaccc taacctggtg    900
cagctccttg gtaggggcct ggccaggcag cctgcgccat ggagtcacag ggcgtggagc    960
cgggcagcct tttacaaaaa gccccagcct aggaggtctc agggcgcagc ttctaacctc   1020
agtgctggca acacattgga ccttggaaca aaggcaaaca ctaggctcct ggcaaagcca   1080
gctttgggca tgcatccagg gctaaattca gccaggccta gactctggac cagtggagca   1140
gctaatcccc ggagggtctg cacccgggag ccccgttct atatcatcac tgagttcatg   1200
acctacggga acctcctgga ctacctgagg gagtgcaacc ggcaggaggt gaacgccgtg   1260
gtgctgctgt acatggccac tcagatctcg tcagccatgg agtacctgga agaaaaaac    1320
ttcatccaca gagatcttgc tgcccgaaac tgcctggtag gggagaacca cttggtgaag   1380
gtagctgatt ttggcctgag caggttgatg acaggggaca cctacacagc ccatgctgga   1440
gccaagttcc ccatcaaatg gactgcaccc gagagcctgg cctacaacaa gttctccatc   1500
aagtccgacg tctgggcatt tggagtattg ctttgggaaa ttgctaccta tggcatgtcc   1560
ccttacccgg gaattgacct gtcccaggtg tatgagctgc tagagaagga ctaccgcatg   1620
gagcgcccag aaggctgccc agagaaggtc tatgaactca tgcgagcatg ttggcagtgg   1680
aatccctctg accggccctc ctttgctgaa atccaccaag cctttgaaac aatgttccag   1740
gaatccagta tctcagacga agtggaaaag gagctgggga acaaggcgt ccgtggggct    1800
gtgagtacct tgctgcaggc cccagagctg cccaccaaga cgaggacctc caggagagct   1860
gcagagcaca gagacaccac tgacgtgcct gagatgcctc actccaaggg ccaggagag    1920
agcgatcctc tggaccatga gcctgccgtg tctccattgc tccctcgaaa agagcgaggt   1980
cccccggagg gcggcctgaa tgaagatgag cgccttctcc caaagacaa aaagaccaac    2040
ttgttcagcg ccttgatcaa gaagaagaag aagacagccc caacccctcc caaacgcagc   2100
agctccttcc gggagatgga cggccagccg gagcgcagag gggccggcga ggaagagggc   2160
cgagacatca gcaacggggc actggctttc acccccttgg acacagctga cccagccaag   2220
tccccaaagc ccagcaatgg ggctgggtc cccaatggag ccctccggga gtccgggggc    2280
tcaggcttcc ggtctcccca cctgtggaag aagtccagca cgctgaccag cagccgccta   2340
gccaccggcg aggaggaggg cggtggcagc tccagcaagc gcttcctgcg ctcttgctcc   2400
```

```
gcctcctgcg ttccccatgg ggccaaggac acggagtgga ggtcagtcac gctgcctcgg    2460
gacttgcagt ccacgggaag acagtttgac tcgtccacat ttggagggca caaaagtgag    2520
aagccggctc tgcctcggaa gagggcaggg gagaacaggt ctgaccaggt gacccgaggc    2580
acagtaacgc ctcccccag gctggtgaaa aagaatgagg aagctgctga tgaggtcttc     2640
aaagacatca tggagtccag cccgggctcc agcccgccca acctgactcc aaaacccctc    2700
cggcggcagg tcaccgtggc ccctgcctcg ggcctccccc acaaggaaga agctggaaag    2760
ggcagtgcct tagggacccc tgctgcagct gagccagtga cccccaccag caaagcaggc    2820
tcaggtgcac caggggcac cagcaagggc cccgccgagg agtccagagt gaggaggcac      2880
aagcactcct ctgagtcgcc agggagggac aaggggaaat tgtccaggct caaacctgcc    2940
ccgccgcccc caccagcagc ctctgcaggg aaggctggag gaaagccctc gcagagcccg    3000
agccaggagg cggccgggga ggcagtcctg ggcgcaaaga caaaagccac gagtctggtt    3060
gatgctgtga acagtgacgc tgccaagccc agccagccgg gagagggcct caaaaagccc    3120
gtgctcccgg ccactccaaa gccacagtcc gccaagccgt cggggacccc catcagccca    3180
gcccccgttc cctccacgtt gccatcagca tcctcggccc tggcagggga ccagccgtct    3240
tccaccgcct tcatccctct catatcaacc cgagtgtctc ttcggaaaac ccgccagcct    3300
ccagagcgga tcgccagcgg cgccatcacc aagggcgtgg tcctggacag caccgaggcg    3360
ctgtgcctcg ccatctctag gaactccgag cagatggcca gccacagcgc agtgctggag    3420
gccggcaaaa acctctacac gttctgcgtg agctatgtgg attccatcca gcaaatgagg    3480
aacaagtttg ccttccgaga ggccatcaac aaactggaga ataatctccg ggagcttcag    3540
atctgcccgg cgacagcagg cagtggtcca gcggccactc aggacttcag caagctcctc    3600
agttcggtga aggaaatcag tgacatagtg cagaggtagc agcagtcagg ggtcaggtgt    3660
caggcccgtc ggagctgcct gcagcacatg cgggctcgcc cataccgtg acagtggctg     3720 acaagggact agtgagtcag caccttggcc caggagctct gcgccaggca gagctgaggg    3780
ccctgtggag tccagctcta ctacctacgt ttgcaccgcc tgcccctccg caccttcctc    3840
ctccccgctc cgtctctgtc ctcgaatttt atctgtggag ttcctgctcc gtggactgca    3900
gtcggcatgc caggacccgc cagccccgct cccaccttagt gccccagact gagctctcca   3960
ggccaggtgg gaacggctga tgtggactgt cttttttcatt tttttctctc tggagcccct   4020
cctcccccgg ctgggcctcc ttcttccact tctccaagaa tggaagcctg aactgaggcc    4080
ttgtgtgtca ggccctctgc ctgcactccc tggccttgcc cgtcgtgtgc tgaagacatg    4140
tttcaagaac cgcatttcgg gaagggcatg cacgggcatg cacacggctg gtcactctgc    4200
cctctgctgc tgcccggggt ggggtgcact cgccatttcc tcacgtgcag acagctctt    4260 gatttgggtg gaaaacaggg tgctaaagcc aaccagcctt gggtcctgg gcaggtggga    4320 gctgaaaagg atcgaggcat ggggcatgtc ctttccatct gtccacatcc ccagagccca    4380
gctcttgctc tcttgtgacg tgcactgtga atcctggcaa gaaagcttga gtctcaaggg    4440
tggcaggtca ctgtcactgc cgacatcct ccccagcag aatggaggca ggggacaagg      4500
gaggcagtgg ctagtggggt gaacagctgg tgccaaatag ccccagactg gcccaggca     4560 ggtctgcaag ggcccagagt gaaccgtcct ttcacacatc tgggtgccct gaagggccc     4620 ttcccctccc ccactcctct aagacaaagt agattcttac aaggcccttt cctttggaac    4680
aagacagcct tcacttttct gagttcttga agcatttcaa agccctgcct ctgtgtagcc    4740
```

```
gccctgagag agaatagagc tgccactggg cacctgcgca caggtgggag gaaagggcct    4800
ggccagtcct ggtcctggct gcactcttga actgggcgaa tgtcttattt aattaccgtg    4860
agtgacatag cctcatgttc tgtggggtc atcagggagg gttaggaaaa ccacaaacgg     4920 agccctgaa agcctcacgt atttcacaga gcacgcctgc catcttctcc ccgaggctgc     4980
cccaggccgg agcccagata cggggggctgt gactctgggc agggacccgg ggtctcctgg   5040
accttgacag agcagctaac tccgagagca gtgggcaggt ggccgcccct gaggcttcac    5100
gccgggagaa gccaccttcc cacccctta taccgcctcg tgccagcagc ctcgcacagg     5160
ccctagcttt acgctcatca cctaaacttg tactttattt ttctgataga aatggtttcc    5220
tctggatcgt tttatgcggt tcttacagca catcacctct ttgcccccga cggctgtgac    5280
gcagccggag ggaggcacta gtcaccgaca gcggccttga agacagagca aagcgcccac    5340
ccaggtcccc cgactgcctg tctccatgag gtactggtcc cttccttttg ttaacgtgat    5400
gtgccactat attttacacg tatctcttgg tatgcatctt ttatagacgc tcttttctaa    5460
gtggcgtgtg catagcgtcc tgccctgccc cctcggggc ctgtggtggc tcccctctg     5520 cttctcgggg tccagtgcat tttgtttctg tatatgattc tctgtggttt ttttgaatc    5580 caaatctgtc ctctgtagta tttttaaat aaatcagtgt ttacatt                  5627
```

<210> SEQ ID NO 5
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Gly Ser Cys Trp
            180                 185
```

<210> SEQ ID NO 6

<211> LENGTH: 1211
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Met Leu Glu Ile Cys Leu Lys Leu Val Gly Cys Lys Ser Lys Lys Gly
1               5                   10                  15

Leu Ser Ser Ser Ser Cys Tyr Leu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
        195                 200                 205

Leu Ile Thr Thr Leu His Tyr Pro Ala Pro Lys Arg Asn Lys Pro Thr
    210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
                245                 250                 255

Tyr Glu Gly Val Trp Lys Lys Tyr Ser Leu Thr Val Ala Val Lys Thr
            260                 265                 270

Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Arg
    290                 295                 300

Gly Leu Ala Arg Gln Pro Ala Pro Trp Ser His Arg Ala Trp Ser Arg
305                 310                 315                 320

Ala Ala Phe Tyr Lys Lys Pro Gln Pro Arg Arg Ser Gln Gly Ala Ala
                325                 330                 335

Ser Asn Leu Ser Ala Gly Asn Thr Leu Asp Leu Gly Thr Lys Ala Asn
            340                 345                 350

Thr Arg Leu Leu Ala Lys Pro Ala Leu Gly Met His Pro Gly Leu Asn
        355                 360                 365

Ser Ala Arg Pro Arg Leu Trp Thr Ser Gly Ala Ala Asn Pro Arg Arg
```

```
              370                 375                 380
Val Cys Thr Arg Glu Pro Pro Phe Tyr Ile Ile Thr Glu Phe Met Thr
385                 390                 395                 400

Tyr Gly Asn Leu Leu Asp Tyr Leu Arg Glu Cys Asn Arg Gln Glu Val
                405                 410                 415

Asn Ala Val Val Leu Leu Tyr Met Ala Thr Gln Ile Ser Ser Ala Met
            420                 425                 430

Glu Tyr Leu Glu Lys Lys Asn Phe Ile His Arg Asp Leu Ala Ala Arg
        435                 440                 445

Asn Cys Leu Val Gly Glu Asn His Leu Val Lys Val Ala Asp Phe Gly
    450                 455                 460

Leu Ser Arg Leu Met Thr Gly Asp Thr Tyr Thr Ala His Ala Gly Ala
465                 470                 475                 480

Lys Phe Pro Ile Lys Trp Thr Ala Pro Glu Ser Leu Ala Tyr Asn Lys
                485                 490                 495

Phe Ser Ile Lys Ser Asp Val Trp Ala Phe Gly Val Leu Leu Trp Glu
            500                 505                 510

Ile Ala Thr Tyr Gly Met Ser Pro Tyr Pro Gly Ile Asp Leu Ser Gln
        515                 520                 525

Val Tyr Glu Leu Leu Glu Lys Asp Tyr Arg Met Glu Arg Pro Glu Gly
    530                 535                 540

Cys Pro Glu Lys Val Tyr Glu Leu Met Arg Ala Cys Trp Gln Trp Asn
545                 550                 555                 560

Pro Ser Asp Arg Pro Ser Phe Ala Glu Ile His Gln Ala Phe Glu Thr
                565                 570                 575

Met Phe Gln Glu Ser Ser Ile Ser Asp Glu Val Glu Lys Glu Leu Gly
            580                 585                 590

Lys Gln Gly Val Arg Gly Ala Val Ser Thr Leu Leu Gln Ala Pro Glu
        595                 600                 605

Leu Pro Thr Lys Thr Arg Thr Ser Arg Arg Ala Ala Glu His Arg Asp
    610                 615                 620

Thr Thr Asp Val Pro Glu Met Pro His Ser Lys Gly Gln Gly Glu Ser
625                 630                 635                 640

Asp Pro Leu Asp His Glu Pro Ala Val Ser Pro Leu Leu Pro Arg Lys
                645                 650                 655

Glu Arg Gly Pro Pro Glu Gly Gly Leu Asn Glu Asp Gly Arg Leu Leu
            660                 665                 670

Pro Lys Asp Lys Lys Thr Asn Leu Phe Ser Ala Leu Ile Lys Lys Lys
        675                 680                 685

Lys Lys Thr Ala Pro Thr Pro Pro Lys Arg Ser Ser Ser Phe Arg Glu
    690                 695                 700

Met Asp Gly Gln Pro Glu Arg Arg Gly Ala Gly Glu Glu Glu Gly Arg
705                 710                 715                 720

Asp Ile Ser Asn Gly Ala Leu Ala Phe Thr Pro Leu Asp Thr Ala Asp
                725                 730                 735

Pro Ala Lys Ser Pro Lys Pro Ser Asn Gly Ala Gly Val Pro Asn Gly
            740                 745                 750

Ala Leu Arg Glu Ser Gly Gly Ser Gly Phe Arg Ser Pro His Leu Trp
        755                 760                 765

Lys Lys Ser Ser Thr Leu Thr Ser Ser Arg Leu Ala Thr Gly Glu Glu
    770                 775                 780

Glu Gly Gly Gly Ser Ser Ser Lys Arg Phe Leu Arg Ser Cys Ser Ala
785                 790                 795                 800
```

-continued

```
Ser Cys Val Pro His Gly Ala Lys Asp Thr Glu Trp Arg Ser Val Thr
            805                 810                 815

Leu Pro Arg Asp Leu Gln Ser Thr Gly Arg Gln Phe Asp Ser Ser Thr
            820                 825                 830

Phe Gly Gly His Lys Ser Glu Lys Pro Ala Leu Pro Arg Lys Arg Ala
            835                 840                 845

Gly Glu Asn Arg Ser Asp Gln Val Thr Arg Gly Thr Val Thr Pro Pro
            850                 855                 860

Pro Arg Leu Val Lys Lys Asn Glu Glu Ala Ala Asp Glu Val Phe Lys
865                 870                 875                 880

Asp Ile Met Glu Ser Ser Pro Gly Ser Ser Pro Asn Leu Thr Pro
            885                 890                 895

Lys Pro Leu Arg Arg Gln Val Thr Val Ala Pro Ala Ser Gly Leu Pro
            900                 905                 910

His Lys Glu Glu Ala Gly Lys Gly Ser Ala Leu Gly Thr Pro Ala Ala
            915                 920                 925

Ala Glu Pro Val Thr Pro Thr Ser Lys Ala Gly Ser Gly Ala Pro Gly
            930                 935                 940

Gly Thr Ser Lys Gly Pro Ala Glu Glu Ser Arg Val Arg Arg His Lys
945                 950                 955                 960

His Ser Ser Glu Ser Pro Gly Arg Asp Lys Gly Lys Leu Ser Arg Leu
            965                 970                 975

Lys Pro Ala Pro Pro Pro Pro Ala Ala Ser Ala Gly Lys Ala Gly
            980                 985                 990

Gly Lys Pro Ser Gln Ser Pro Ser Gln Glu Ala Ala Gly Glu Ala Val
            995                 1000                1005

Leu Gly Ala Lys Thr Lys Ala Thr Ser Leu Val Asp Ala Val Asn
            1010                1015                1020

Ser Asp Ala Ala Lys Pro Ser Gln Pro Gly Glu Gly Leu Lys Lys
            1025                1030                1035

Pro Val Leu Pro Ala Thr Pro Lys Pro Gln Ser Ala Lys Pro Ser
            1040                1045                1050

Gly Thr Pro Ile Ser Pro Ala Pro Val Pro Ser Thr Leu Pro Ser
            1055                1060                1065

Ala Ser Ser Ala Leu Ala Gly Asp Gln Pro Ser Ser Thr Ala Phe
            1070                1075                1080

Ile Pro Leu Ile Ser Thr Arg Val Ser Leu Arg Lys Thr Arg Gln
            1085                1090                1095

Pro Pro Glu Arg Ile Ala Ser Gly Ala Ile Thr Lys Gly Val Val
            1100                1105                1110

Leu Asp Ser Thr Glu Ala Leu Cys Leu Ala Ile Ser Arg Asn Ser
            1115                1120                1125

Glu Gln Met Ala Ser His Ser Ala Val Leu Glu Ala Gly Lys Asn
            1130                1135                1140

Leu Tyr Thr Phe Cys Val Ser Tyr Val Asp Ser Ile Gln Gln Met
            1145                1150                1155

Arg Asn Lys Phe Ala Phe Arg Glu Ala Ile Asn Lys Leu Glu Asn
            1160                1165                1170

Asn Leu Arg Glu Leu Gln Ile Cys Pro Ala Thr Ala Gly Ser Gly
            1175                1180                1185

Pro Ala Ala Thr Gln Asp Phe Ser Lys Leu Leu Ser Ser Val Lys
            1190                1195                1200
```

Glu Ile Ser Asp Ile Val Gln Arg
    1205            1210

<210> SEQ ID NO 7
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gggagctgct ggtgaggatt attttagact gtgagtaatt gacctgacag acagtgatga    60
ctgcttcatt aagagcccac gaccacgtgc cagaatagtt cagcatcctc tgttgctact   120
gtactttgag acatcgttct tctttgtgat gcaatacctc tttcttgtca tgagggtctc   180
ttcccttaaa tcagg                                                    195

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ala Ser Asp Gly Lys Gly Ser Cys Trp
1               5                   10

<210> SEQ ID NO 9
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9 gtagggcct ggccaggcag cctgcgccat ggagtcacag ggcgtggagc cggcagcct      60 tttacaaaaa gccccagcct aggaggtctc agggcgcagc ttctaacctc agtgctggca   120
acacattgga ccttggaaca aaggcaaaca ctaggctcct ggcaaagcca gctttgggca   180
tgcatccagg gctaaattca gccaggccta gactctggac cagtggagca gctaatcccc   240
gga                                                                 243

<210> SEQ ID NO 10
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Arg Gly Leu Ala Arg Gln Pro Ala Pro Trp Ser His Arg Ala Trp Ser
1               5                   10                  15

Arg Ala Ala Phe Tyr Lys Lys Pro Gln Pro Arg Ser Gln Gly Ala
                20                  25                  30

Ala Ser Asn Leu Ser Ala Gly Asn Thr Leu Asp Leu Gly Thr Lys Ala
        35                  40                  45

Asn Thr Arg Leu Leu Ala Lys Pro Ala Leu Gly Met His Pro Gly Leu
    50                  55                  60

Asn Ser Ala Arg Pro Arg Leu Trp Thr Ser Gly Ala Ala Asn Pro Arg
 65                  70                  75                  80

Arg

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggcaagggga g                                                              11

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atcaggctct ac                                                             12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tccttggtag gg                                                             12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cccggagggt ct                                                             12

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgaccaactc gtgtgtgaaa ctc                                                 23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 16
tccacttcgt ctgagatact ggatt                                          25

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgcaacaagc ccactgtct                                                 19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caagtggttc tcccctacca                                                20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tggtagggga gaaccacttg                                                20
```

BCR-ABL1 SPLICE VARIANTS AND USES THEREOF

FIELD OF THE INVENTION

The present invention relates to BCR-ABL1 variants and resistance to kinase inhibitor therapy.

BACKGROUND OF THE INVENTION

The following description is provided to assist the understanding of the reader. None of the information provided or references cited is admitted to be prior art to the present invention.

Chronic Myelogenous Leukemia ("CML") is a cancer of bone marrow and blood cells. In CML, healthy bone marrow cells are replaced with leukemic cells; myeloid, erythroid, megakaroyocytic and B lymphoid cells are among the blood cells which become leukemic due to the effects of a characteristic chromosomal translocation.

CML is associated with a specific chromosomal abnormality called Philadelphia chromosome. The genetic defect is caused by the reciprocal translocation designated t(9;22)(q34;q11), which refers to an exchange of genetic material between region q34 of chromosome 9 and region q11 of chromosome 22 (Rowley, J. D. *Nature.* 1973; 243: 290-3; Kurzrock et al. *N. Engl. J. Med.* 1988; 319: 990-998). This translocation results in a portion of the bcr ("breakpoint cluster region") gene from chromosome 22 (region q11) becoming fused with a portion of the abl1 gene on chromosome 9 (region q34). (Wong & Witte, *Annu. Rev. Immunol.* 2004; 22: 247-306).

The fused "bcr-abl" gene is located on chromosome 22, which is shortened as a result of the translocation. The fused gene retains the tyrosine kinase domain of the abl gene, which is constitutively active (Elefanty et al. *EMBO J.* 1990; 9: 1069-1078). This kinase activity activates various signal transduction pathways leading to uncontrolled cell growth and division (e.g., by promoting cell proliferation and inhibiting apoptosis). For example, BCR-ABL may cause undifferentiated blood cells to proliferate and fail to mature.

Alternative bcr-abl1 splice variants in Philadelphia chromosome-positive CML patient have been reported. Specifically, alternative splice variants between BCR exon 1, 13 and ABL exon 4 or 5 were reported by Volpe et al., (*Cancer Res.* 67:5300-07 (2007).

Treatment of CML may involve drug therapy (e.g., chemotherapy), bone marrow transplants, or combinations of both. One class of drugs that may be used for treating CML is kinase inhibitors. For example, "imatinib mesylate" (also known as STI571 or 2-phenylaminopyrimidine or "Imatinib") has proven effective for treating CML (Deininger et al., *Blood.* 1997; 90: 3691-3698; Manley, P. W., *Eur. J. Cancer.* 2002; 38: S19-S27). Imatinib is marketed as a drug under the trade name "Gleevec" or "Glivec." Other examples of kinase inhibitor drugs for treating CML include nilotinib, dasatinib, Bosutinib (SKI-606) and Aurora kinase inhibitor VX-680.

Imatinib is an ATP competitive inhibitor of BCR-ABL1 kinase activity and functions by binding to the kinase domain of BCR-ABL1 and stabilizing the protein in its closed, inactive conformation. Monotherapy with imatinib has been shown to be effective for all stages of CML.

Resistance to imatinib, and other kinase inhibitors, remains a major problem in the management of patients with CML. Rates at which primary (failure to achieve any hematologic response) and secondary resistance (i.e., hematologic recurrence) occurs varies dependent on the stage of diseases. Primary resistance has been reported in chronic-, accelerated-, or blast-phase at rates of 3%, 9%, and 51%, respectively (Melo, J. V. & Chuah, *C. Cancer Lett.* 2007; 249: 121-132; Hughes, T. *Blood.* 2006; 108: 28-37). Secondary resistance has been reported in these patients at rates of 22%, 32%, and 41%, respectively.

The complete mechanism of kinase inhibitor resistance in CML patients is unclear and a significant number of patients resistant to imatinib have no mutation in the bcr-abl1 gene. However, 35-45% of patients with imatinib resistance have mutations in the kinase domain of the BCR-ABL1 protein (Mahon, F. X. *Blood.* 2000; 96: 1070-1079). Most of the reported mutations disrupt critical contact points between imatinib and the tyrosine kinase receptor or induce a transition from the inactive to the active protein configuration, preventing imatinib binding (Nagar, B. *Cell.* 2003; 112: 859-871; Nagar et al., *Cancer Res.* 2002; 62: 4236-4243; Branford S. *Blood.* 2002; 99: 3472-3475; Branford et al. *Blood.* 2003; 102: 276-283; O'Hare et al., *Blood* 2007 110: 2242-2249 (2007)).

The T315I mutation (Gone et al. *Science.* 2001; 293: 876-880; Hochhaus et al. *Leukemia.* 2002; 16: 2190-2196) and some mutations affecting the P-loop of BCR-ABL1 confer a greater level of resistance to imatinib (Branford et al. *Blood.* 2002; 99: 3472-3475; Branford et al. *Blood.* 2003; 102: 276-283; and Gone et al. *Blood.* 2002; 100: 3041-3044) as well as other tyrosine kinase inhibitors that are currently used and tested in these patients (Hughes et al. *Blood.* 2006; 108: 28-37; Hochhaus, et al. *Blood.* 2006; 108: 225a). The role of Src family kinases has received particular interest as possible mechanism for imatinib resistance (Levinson et al. *PLoS Biol.* 2006; 4: e144). Overexpression and activation of the Lyn has been implicated in imatinib-resistance (Donato, N. J. *Blood.* 2003; 101: 690-698).

Furthermore, Chu et al. (*N. Engl. J. Med.* 2006; 355: 10) describe an insertion/truncation mutant of BCR-ABL1 in a CML patient resistant to imatinib. Chu et al. report that the mutant results from a 35 base insertion of abl1 intron 8 into the junction between exons 8 and 9, resulting in a new C-terminus and truncation of the normal C-terminus of the ABL1 portion of the fusion protein. Laudadio et al. (*J. Mol. Diag.* 2008; 10(2): 177-180) and Lee et al. (*Mol. Cancer Ther.* 2008; 7(12): 3834-41) also report a similar splice variant in CML patients that had undergone imatinib therapy. An additional splice variant without c-ABL exon 7 has also been reported in Imatinib-resistant patients. Curvo et al., *Leuk. Res.* 2007; 32:508-510.

SUMMARY OF THE INVENTION

The present inventions are based on bcr-abl1 splice variants which result from insertion and/or truncation of the bcr-abl1 transcript and the finding that these variants provide resistance to kinase domain inhibitors such as imatinib, nilotinib and dasatinib.

In one aspect, the invention provides a method for predicting likelihood for resistance of a patient with a bcr-abl1 translocation to treatment with one or more BCR-ABL1 kinase inhibitors, comprising: (a) assessing the bcr-abl1 mRNA in a sample obtained from the patient for the presence or absence of a polynucleotide sequence encoding the 1951NS bcr-abl1 splice variant or the 243INS bcr-abl1 splice variant; and (b) identifying the patient as having an increased likelihood of being resistant to treatment with one or more BCR-ABL1 kinase inhibitors when a polynucleotide encoding at least one of said splice variants is detected.

In some embodiments, the presence or absence of the 195INS bcr-abl1 splice variant is determined by detecting the presence or absence of a bcr-abl1 nucleic acid comprising the sequence of SEQ ID NO: 3.

In another aspect, the invention provides a method for predicting likelihood for resistance of a patient with a bcr-abl1 translocation to treatment with one or more BCR-ABL1 kinase inhibitors, comprising: (a) assessing the BCR-ABL1 protein in a sample obtained from a patient for the presence or absence of a truncated Abl protein encoded by the 195INS bcr-abl1 splice variant or the protein encoded by the 243INS bcr-abl1 splice variant; and (b) identifying the patient as having an increased likelihood of being resistant to treatment with one or more BCR-ABL1 kinase inhibitors when at least one of said truncated proteins is detected.

In some embodiments, the presence or absence of the BCR-ABL1 protein encoded by the bcr-abl1 splice variants is determined by detecting the size of the BCR-ABL1 protein(s) in the patient sample, or by using an antibody that specifically binds to the BCR-ABL1 protein encoded by the 195INS bcr-abl1 splice variant or the 243INS bcr-abl1 splice variant, or by sequencing the C-terminus of the BCR-Abl protein. In some embodiments, the C-terminus of the Abl protein encoded the 195INS bcr-abl1 splice variant comprises the amino acid sequence of SEQ ID NO: 5 and/or the Abl protein encoded by the 243INS bcr-abl splice variant comprising the amino acid sequence of SEQ ID NO: 6.

In some embodiments of either of the foregoing aspects, the patient is diagnosed as having a myeloproliferative disease (e.g., chronic myelogenous leukemia (CML)). In other embodiments, the kinase inhibitors include one or more of imatinib, nilotinib, bosutinib, and dasatinib. In other embodiments, the sample is a blood or bone marrow. Preferably, the sample contains blood cells (e.g., peripheral mononuclear cells) and/or platelets.

In another aspect, the invention provides a recombinant polynucleotide which encodes the 195INS bcr-abl1 splice variant or the 243INS bcr-abl1 splice variant. In some embodiment, the recombinant polynucleotide is operably linked to an expression regulatory element capable of modulating the expression of said recombinant polynucleotide. The regulatory element optionally contains a promoter, an enhancer, and/or a poly-adenylation signal. The vectors include expression vectors and may be eukaryotic, prokaryotic, or viral.

The term "myeloproliferative disease" as used herein means a disorder of a bone marrow-derived cell type, such as a white blood cell. A myeloproliferative disease is generally manifest by abnormal cell division resulting in an abnormal level of a particular hematological cell population. The abnormal cell division underlying a myeloproliferative disease is typically inherent in the cells and not a normal physiological response to infection or inflammation. A leukemia is a type of myeloproliferative disease. Exemplary myeloproliferative disease include, but are not limited to, acute myeloid leukemia, acute lymphoblastic leukemia, chronic lymphocytic leukemia, myelodysplastic syndrome, chronic myeloid leukemia, hairy cell leukemia, leukemic manifestations of lymphomas, and multiple myeloma.

As used herein, the term "sample" or "biological sample" refers to any liquid or solid material obtained from a biological source, such a cell or tissue sample or bodily fluids. "Bodily fluids" may include, but are not limited to, blood, serum, plasma, saliva, cerebrospinal fluid, pleural fluid, tears, lactal duct fluid, lymph, sputum, urine, saliva, amniotic fluid, and semen. A sample may include a bodily fluid that is "acellular." An "acellular bodily fluid" includes less than about 1% (w/w) whole cellular material. Plasma or serum are examples of acellular bodily fluids. A sample may include a specimen of natural or synthetic origin.

"Nucleic acid" or "nucleic acid sequence" as used herein refers to an oligonucleotide, nucleotide or polynucleotide, and fragments or portions thereof, which may be single or double stranded, and represent the sense or antisense strand. A nucleic acid may include DNA or RNA, and may be of natural or synthetic origin and may contain deoxyribonucleotides, ribonucleotides, or nucleotide analogs in any combination.

Non-limiting examples of polynucleotides include a gene or gene fragment, genomic DNA, exons, introns, mRNA, tRNA, rRNA, ribozymes, cDNA, recombinant polynucleotides, branched polynucleotides, plasmids, vectors, isolated DNA of any sequence, isolated RNA of any sequence, synthetic nucleic acid, nucleic acid probes and primers. Polynucleotides may be natural or synthetic. Polynucleotide may comprise modified nucleotides, such as methylated nucleotides and nucleotide analogs, uracyl, other sugars and linking groups such as fluororibose and thiolate, and nucleotide branches. A nucleic acid may be modified such as by conjugation, with a labeling component. Other types of modifications included in this definition are caps, substitution of one or more of the naturally occurring nucleotides with an analog, and introduction of chemical entities for attaching the polynucleotide to other molecules such as proteins, metal ions, labeling components, other polynucleotides or a solid support. Nucleic acid may include a nucleic acid that has been amplified (e.g., using polymerase chain reaction).

A fragment of a nucleic acid generally contains at least about 15, 20, 25, 30, 35, 40, 45, 50, 75, 100, 200, 300, 400, 500, 1000 nucleotides or more. Larger fragments are possible and may include about 2,000, 2,500, 3,000, 3,500, 4,000, 5,000 7,500, or 10,000 bases.

"Gene" as used herein refers to a DNA sequence that comprises control and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained.

Although a sequence of the nucleic acids may be shown in the form of DNA, a person of ordinary skill in the art recognizes that the corresponding RNA sequence will have a similar sequence with the thymine being replaced by uracil, i.e. "t" with "u".

"Identity" and "identical" as used herein refer to a degree of identity between sequences. There may be partial identity or complete identity. A partially identical sequence is one that is less than 100% identical to another sequence. Preferably, partially identical sequences have an overall identity of at least 70% or at least 75%, more preferably at least 80% or at least 85%, most preferably at least 90% or at least 95% or at least 99%. Sequence identity determinations may be made for sequences which are not fully aligned. In such instances, the most related segments may be aligned for optimal sequence identity by and the overall sequence identity reduced by a penalty for gaps in the alignment.

"Hybridize" or "hybridization" as used herein refers to the pairing of substantially complementary nucleotide sequences (strands of nucleic acid) to form a duplex or heteroduplex through formation of hydrogen bonds between complementary base pairs. Hybridization and the strength of hybridization (i.e., the strength of the association between the nucleic acids) is influenced by such factors as the degree of complementary between the nucleic acids, stringency of the conditions involved, and the thermal melting point ($T_m$) of the formed hybrid. An oligonucleotide or polynucleotide (e.g., a probe or a primer) that is specific for a target nucleic acid will "hybridize" to the target nucleic acid under suitable conditions.

"Specific hybridization" as used herein refers to an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the $T_m$ for the specific sequence at a defined ionic strength and pH. The $T_m$ is the temperature (under defined ionic strength and pH) at which 50% of the target sequence hybridizes to a perfectly matched probe. Equations for calculating $T_m$ and conditions for nucleic acid hybridization are known in the art.

"Stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

"Substantially complementary" as used herein refers to two sequences that hybridize under stringent hybridization conditions. The skilled artisan will understand that substantially complementary sequences need not hybridize along their entire length.

Oligonucleotides can be used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

"Oligonucleotide" as used herein refers to a molecule that has a sequence of nucleic acid bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group in this position. Oligonucleotides also may include derivatives, in which the hydrogen of the hydroxyl group is replaced with organic groups, e.g., an allyl group. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, reverse transcription, PCR, or a combination thereof. The oligonucleotide may be modified. For example, the oligonucleotide may be labeled with an agent that produces a detectable signal (e.g., a fluorophore).

"Primer" as used herein refers to an oligonucleotide that is capable of acting as a point of initiation of synthesis when placed under conditions in which primer extension is initiated (e.g., primer extension associated with an application such as PCR). The primer is complementary to a target nucleotide sequence and it hybridizes to a substantially complementary sequence in the target and leads to addition of nucleotides to the 3'-end of the primer in the presence of a DNA or RNA polymerase. The 3'-nucleotide of the primer should generally be complementary to the target sequence at a corresponding nucleotide position for optimal expression and amplification. An oligonucleotide "primer" may occur naturally, as in a purified restriction digest or may be produced synthetically. The term "primer" as used herein includes all forms of primers that may be synthesized including peptide nucleic acid primers, locked nucleic acid primers, phosphorothioate modified primers, labeled primers, and the like.

Primers are typically between about 10 and about 100 nucleotides in length, preferably between about 15 and about 60 nucleotides in length, more preferably between about 20 and about 50 nucleotides in length, and most preferably between about 25 and about 40 nucleotides in length. In some embodiments, primers can be at least 8, at least 12, at least 16, at least 20, at least 25, at least 30, at least 35, at least 40, at least 45, at least 50, at least 55, at least 60 nucleotides in length. An optimal length for a particular primer application may be readily determined in the manner described in H. Erlich, PCR Technology, Principles and Application for DNA Amplification (1989).

"Probe" as used herein refers to nucleic acid that interacts with a target nucleic acid via hybridization. A probe may be fully complementary to a target nucleic acid sequence or partially complementary. The level of complementarity will depend on many factors based, in general, on the function of the probe. A probe or probes can be used, for example to detect the presence or absence of a mutation in a nucleic acid sequence by virtue of the sequence characteristics of the target. Probes can be labeled or unlabeled, or modified in any of a number of ways well known in the art. A probe may specifically hybridize to a target nucleic acid.

Probes may be DNA, RNA or a RNA/DNA hybrid. Probes may be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified internucleotide linkages. A probe may be fully complementary to a target nucleic acid sequence or partially complementary. A probe may be used to detect the presence or absence of a target nucleic acid. Probes are typically at least about 10, 15, 20, 25, 30, 35, 40, 50, 60, 75, 100 nucleotides or more in length.

"Detecting" as used herein refers to determining the presence of a nucleic acid of interest in a sample or the presence of a protein of interest in a sample. Detection does not require the method to provide 100% sensitivity and/or 100% specificity.

"Detectable label" as used herein refers to a molecule or a compound or a group of molecules or a group of compounds used to identify a nucleic acid or protein of interest.

In some cases, the detectable label may be detected directly. In other cases, the detectable label may be a part of a binding pair, which can then be subsequently detected. Signals from the detectable label may be detected by various means and will depend on the nature of the detectable label. Detectable labels may be isotopes, fluorescent moieties, colored substances, and the like. Examples of means to detect detectable label include but are not limited to spectroscopic, photochemical, biochemical, immunochemical, electromagnetic, radiochemical, or chemical means, such as fluorescence, chemifluoresence, or chemiluminescence, or any other appropriate means.

"TaqMan® PCR detection system" as used herein refers to a method for real time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

"Vector" as used herein refers to a recombinant DNA or RNA plasmid or virus that comprises a heterologous polynucleotide capable of being delivered to a target cell, either in vitro, in vivo or ex-vivo. The polynucleotide can comprise a sequence of interest and can be operably linked to another nucleic acid sequence such as promoter or enhancer and may control the transcription of the nucleic acid sequence of interest. As used herein, a vector need not be capable of replication in the ultimate target cell or subject. The term vector may include expression vector and cloning vector.

Suitable expression vectors are well-known in the art, and include vectors capable of expressing a polynucleotide operatively linked to a regulatory sequence, such as a promoter region that is capable of regulating expression of such DNA. Thus, an "expression vector" refers to a recombinant DNA or RNA construct, such as a plasmid, a phage, recombinant virus or other vector that, upon introduction into an appropriate host cell, results in expression of the inserted DNA. Appropriate expression vectors include those that are replicable in eukaryotic cells and/or prokaryotic cells and those that remain episomal or those which integrate into the host cell genome.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene, and the ability to enter and/or replicate in eukaryotic or prokaryotic cells. Additionally elements may also be included in the vector such as signal sequences, splice signals, as well as transcriptional promoters, enhancers, and termination signals.

Examples of suitable vectors include, but are not limited to plasmids pcDNA3, pHCMV/Zeo, pCR3.1, pEF I/His, pEMD/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.).

"Promoter" as used herein refers to a segment of DNA that controls transcription of polynucleotide to which it is operatively linked. Promoters, depending upon the nature of the regulation, may be constitutive or regulated. Exemplary eukaryotic promoters contemplated for use in the practice of the present invention include the SV40 early promoter, the cytomegalovirus (CMV) major immediate-early promoter, the mouse mammary tumor virus (MMTV) steroid-inducible promoter, Moloney murine leukemia virus (MMLV) promoter. Exemplary promoters suitable for use with prokaryotic hosts include T7 promoter, beta-lactamase promoter, lactose promoter systems, alkaline phosphatase promoter, a tryptophan (trp) promoter system, and hybrid promoters such as the tac promoter.

"Antibody" as used herein refers to a polypeptide, at least a portion of which is encoded by at least one immunoglobulin gene, or fragment thereof, and that can bind specifically to a desired target molecule. The term includes naturally-occurring forms, as well as fragments and derivatives. Fragments within the scope of the term "antibody" include those produced by digestion with various proteases, those produced by chemical cleavage and/or chemical dissociation, and those produced recombinantly, so long as the fragment remains capable of specific binding to a target molecule. Among such fragments are Fab, Fab', Fv, F(ab)'2, and single chain Fv (scFv) fragments. Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., Marasco (ed.), *Intracellular Antibodies: Research and Disease Applications*, Springer-Verlag New York, Inc. (1998) (ISBN: 3540641513). As used herein, antibodies can be produced by any known technique, including harvest from cell culture of native B lymphocytes, harvest from culture of hybridomas, recombinant expression systems, and phage display.

"Specifically binds to a polypeptide" as used herein in the context of an antibody refers to binding of an antibody specifically to certain epitope of a polypeptide such that the antibody can distinguish between two proteins with and without such epitope.

BRIEF DESCRIPTION OF THE DRAWINGS

FIG. 1 shows the mRNA sequence of the human abl1 gene as provided in GenBank Accession No.: NM_005157.3 (SEQ ID NO: 1).

FIG. 2 shows the amino acid sequence for human ABL1 protein (SEQ ID NO: 2) as provided in GenBank Accession No: NM_005157.3.

FIG. 3 shows the mRNA sequence of the 195INS abl1 splice variant (SEQ ID NO: 3). The 195 bp insertion is underlined.

FIG. 4 show the mRNA sequence of the 243INS abl1 splice variant (SEQ ID NO: 4). The 243 bp insertion is underlined.

FIG. 5A shows the amino acid sequence encoded by the 195INS abl1 splice variant (SEQ ID NO: 5); FIG. 5B shows the amino acid sequence encoded by the 243INS abl1 splice variant (SEQ ID NO: 6). The amino acids that differ from the non-variant protein are underlined.

FIG. 6 shows the relative frequency of individual BCR-ABL kinase domain mutations detected in a group of 245 patients, 219 of which have CML and 26 of which have Ph-positive acute lymphoblastic leukemia. The numbering of amino acids is based on the Abl protein variant B (which includes ABL exon 1b but not exon 1a). At some positions,

DETAILED DESCRIPTION OF THE INVENTION

BCR-ABL1

The inventions described herein include polynucleotides which encode all or portions of the splice variants in the bcr-abl1 gene product, cells that express all or portions of those splice variants, and proteins encoded by those splice variants. Recombinant cells expressing the truncated BCR-ABL protein with an active kinase domain are useful for identifying drug candidates for treating CML. Methods for predicting likelihood for responsiveness to kinase inhibitor therapy are included along with methods, compositions and reagents for detecting the splice variants. The genomic sequence of the abl1 gene is known, and may be found in GenBank Accession No: NT_035014., from nucleotides 487,774 to 538,010. The genomic sequence of the her gene is also known and may be found at NG_009244.1.

Variants of the bcr-abl1 mRNA

Several splice variants of bcr-abl1 mRNA have been reported. Many of the known sequences are full length cDNA sequences and some are partial cDNA sequences. For example bcr-abl1 mRNA sequences include: NCBI GenBank accession numbers: EU216072, EU216071, EU216070, EU216069, EU216068, EU216067, EU216066, EU216065, EU216064, EU216063, EU216062, EU216061, EU216060, EU216059, EU216058, EU236680, DQ912590, DQ912589, DQ912588, DQ898315, DQ898314, DQ898313, EF423615, EF158045, 572479, 572478, AY789120, AB069693, AF487522, AF113911, AF251769, M30829, M30832, M17542, M15025, and M17541.

Additionally, BCR-ABL1 variant protein sequences have been reported, for example NCBI protein database accession numbers: ABX82708, ABX82702, AAA35594.

CML patients undergoing BCR-ABL1 tyrosine kinase inhibitor therapy may develop resistance to the therapy. The resistance in patients has been associated with mutant splice variant forms of BCR-ABL1. For example, an insertion/truncation mutant of BCR-ABL1 in a CML patient resistant to imatinib has been reported which results from a 35 base insertion of abl intron 8 into the junction between exons 8 and 9 of the bcr-abl mRNA due to alternate splicing (see, for example, Laudadio et al. J. Molec. Diag. 10: 177-180, 2008).

195INS Splice Variant

This splice mutation resulted from the insertion of 195 nucleotides from abl1 intron 4 into the abl1 exon 4-5 junction, and causes a frameshift and protein truncation (FIGS. 3 and 5A). The intron 4 nucleotide sequence inserted by the alternate splicing is:

```
gggagctgct ggtgaggatt attttagactgtgagtaatt gacctgacag acagtgatga (SEQ ID NO: 7)

ctgcttcatt aagagcccac gaccacgtgccagaatagtt cagcatcctc tgttgctact gtactttgag acatcgttct tctttgtgatgcaataacctc tttcttgtca tgagggtctc ttcccttaaa tcagg
```

The inserted sequence results in a non-native ABL1 protein C-terminus having the following amino acid sequence:

```
--TASDGKGSCW     (SEQ ID NO: 8)
```

Because the insertion only affects the abl1 portion of bcr-abl1 translocations, FIGS. 1-5 only show the sequence of abl1 mRNA and resulting protein, and not the entire bcr-abl1 translocation and resulting fusion protein sequences.

Included in the invention are oligonucleotides, primers or probes which are designed to be complementary to some or all of the above sequence or to be complementary to some or all of the above sequence and to some adjoining sequence (not shown) in the mRNA (i.e., a junction sequence). Such oligonucleotides primers or probes can be readily designed so as to hybridize under stringent conditions to 195INS splice variants but not hybridize to the regular bcr-abl1 mRNA or to any other known bcr-abl1 insertion splice variants.

243INS Splice Variant

This splice mutation comprised an 243-nucleotide sequence from intron 6 inserted into the abl1 exon 6-7 junction, causing an insertion of 85 amino acids (FIGS. 4 and 5B). The intron 6 nucleotide sequence inserted by the alternate splicing is:

```
gtaggggcct ggccaggcag cctgcgccat ggagtcacag ggcgtggagc cgggcagcct(SEQ ID NO: 9)

tttacaaaaa gccccagcct aggaggtctc agggcgcagc ttctaacctc agtgctggca acacattgga ccttggaaca aaggcaaaca ctaggctcct ggcaaagcca gctttgggca tgcatccagg gctaaattca gccaggccta gactctggac cagtggagca gctaatcccc gga
```

The amino acid sequence that is inserted in the 243INS splice variant protein is:

```
RGLARQPAPW SHRAWSRAAFYKKPQPRRSQ GAASNLSAGN TLDLGTKANT RLLAKPALGM (SEQ ID NO: 10)
HPGLNSARPR LWTSGAANPRR
```

Because the insertion only affects the abl1 portion of bcr-abl1 translocations, FIGS. 1-5 only show the sequence of abl1 mRNA and resulting protein, and not the entire bcr-abl1 translocation and resulting fusion protein sequences.

Included in the invention are oligonucleotides, primers or probes which are designed to be complementary to some or all of the 243 nucleotides from intron 6 that are present in the mRNA (or cDNA) or which are designed to be complementary to some or all of the 243 nucleotides and to some adjoining sequence in the mRNA (i.e., a junction sequence). Such probes can be readily designed so as to hybridize under stringent conditions to 243INS splice variants but not hybridize to the regular bcr-abl1 mRNA or any other known bcr-abl1 insertion splice variants.

Mutations in the ABL Kinase Domain:

CML patients undergoing tyrosine kinase inhibitor therapy (such as, imatinib, nilotinib, dasatinib, Bosutinib (SKI-606) and Aurora kinase inhibitor VX-680) may develop resistance to such inhibitors. Several underlying mechanisms of resistance to kinase inhibitors have been identified. One major cause is the presence of point mutations within the ABL kinase domain of BCR-ABL1. In one embodiment, such mutations inhibit the ability of imatinib to bind to BCR-ABL1 by altering the binding sites or preventing the kinase domain from assuming the inactive conformation required for imatinib binding (O'Hare et al. Blood. 2007; 110: 2242-2249). Point mutations develop in approximately 35% to 70% of patients displaying resistance to imatinib, either spontaneously or through the evolutionary pressure of imatinib (Branford et al. Blood. 2003; 102: 276-283).

More than 40 distinct resistance-conferring mutations have been detected; the majority fall within four regions of the kinase domain: the ATP-binding loop (P-loop) of the ABL kinase domain, the contact site, the SHY binding site (activation loop), and the catalytic domain (Hughes et al. Blood. 2006; 108: 28-37). A list of such mutations are shown in FIG. 6 and incorporated herein by reference. Approximately 85% of all imatinib-resistant mutations are associated with amino acid substitutions at just seven residues (P-loop: M244V, G250E, Y253F/H and E255K/V; contact site: T315I; and catalytic domain: M351T and F359V). The most frequently mutated region of BCR-ABL is the P-loop, accounting for 36% to 48% of all mutations.

The importance of P-loop mutations is further underlined by in vitro evidence suggesting that these mutations are more oncogenic with respect to un-mutated BCR-ABL as well as other mutated variants. In various biological assays, P-loop mutants Y253F and E255K exhibited an increased transformation potency relative to un-mutated BCR-ABL. Overall, the relative transformation potencies of various mutations were found to be as follows: Y253F>E255K>native BCR-ABL≥T315I>H396P>M351T. Transformation potency also correlated with intrinsic BCR-ABL kinase activity in this study.

In some embodiments, CML patients undergoing kinase inhibitor therapy may develop two kinds of mutations: a) an insertion/truncation mutant of BCR-ABL due to alternate splicing and b) one or more point mutations in the kinase domain of Abl.

In preferred embodiments, the alternate splice variant of bcr-abl1 mRNA can be detected simultaneously with the detection of mutations in abl portion of bcr-abl1 mRNA. In another embodiment, the mutations in the abl portion of bcr-abl1 mRNA can be detected separately. Several methods are known in the art for detection of the presence or absence of such mutations. Non-limiting examples include, DNA sequencing, detection by hybridization of a detectably labeled probe, detection by size, allele specific PCR, ligation amplification reaction (LAR), detection by oligonucleotide arrays.

Biological Sample Collection and Preparation

Sample: Samples, for use in the methods of the present invention, may be obtained from an individual who is suspected of having a disease, e.g. CML, or a genetic abnormality, or who has been diagnosed with CML. Samples may also be obtained from a healthy individual who is assumed of having no disease, e.g. CML, or genetic abnormality. Additionally, the sample may be obtained from CML patients undergoing kinase inhibitor therapy or from CML patients not undergoing kinase inhibitor therapy.

Sample Collection: Methods of obtaining samples are well known to those of skill in the art and include, but are not limited to, aspirations, tissue sections, drawing of blood or other fluids, surgical or needle biopsies, collection of paraffin embedded tissue, collection of body fluids, collection of stool, urine, buccal swab and the like.

Methods of plasma and serum preparation are well known in the art. Either "fresh" blood plasma or serum, or frozen (stored) and subsequently thawed plasma or serum may be used. Frozen (stored) plasma or serum should optimally be maintained at storage conditions of −20 to −70 degrees centigrade until thawed and used. "Fresh" plasma or serum should be refrigerated or maintained on ice until used. Exemplary methods of preparation are described below.

DNA/RNA/Protein Purification

Polynucleotides (e.g., DNA or RNA) or polypeptides may be isolated from the sample according to any methods well known to those of skill in the art. If necessary, the sample may be collected or concentrated by centrifugation and the like. The sample may be subjected to lysis, such as by treatments with enzymes, heat, surfactants, ultrasonication, or a combination thereof. The lysis treatment is performed in order to obtain a sufficient amount of nucleic acid or polypeptide. The sample may be subjected to liquid chromatography to partially purify the nucleic acid or polypeptide. In some embodiments, the whole cell lysates or tissue homogenate may used as source of nucleic acid or polypeptide without further isolation and purification.

Suitable DNA isolation methods include phenol and chloroform extraction, see Sambrook, et al., *Molecular Cloning: A Laboratory Manual* (1989), Second Edition, Cold Spring Harbor Press, Plainview, N.Y.

Numerous commercial kits also yield suitable DNA including, but not limited to, QIAamp™ mini blood kit, Agencourt Genfind™, Roche Cobas® Roche MagNA Pure® or phenol: chloroform extraction using Eppendorf Phase Lock Gels®. Total DNA (e.g., genomic, mitochondrial, microbial, viral,) can be purified from any biological sample such as whole blood, plasma, serum, buffy coat, bone marrow, other body fluids, lymphocytes, cultured cells, tissue, and forensic specimens using commercially available kits e.g., QIAamp DNA and QIAamp DNA Blood mini kits from Qiagen.

In another embodiment, the polynucleotide may be mRNA or cDNA generated from mRNA or total RNA. RNA is isolated from cells or tissue samples using standard techniques, see, e.g., Sambrook, et al., *Molecular Cloning: A Laboratory Manual*, Second Edition (1989), Cold Spring Harbor Press, Plainview, N.Y. In addition, reagents and kits for isolating RNA from any biological sample such as whole blood, plasma, serum, buffy coat, bone marrow, other body fluids, lymphocytes, cultured cells, tissue, and forensic specimens are commercially available e.g., RNeasy Protect Mini kit, RNeasy Protect Cell Mini kit, QIAamp RNA Blood Mini kit, RNeasy Protect Saliva Mini kit, Paxgene Blood RNA kit from Qiagen; MELT™, RNaqueous®, ToTALLY RNA™, RiboPure™-Blood, Poly(A)Purist™ from Applied Biosystems; TRIZOL® reagent, Dynabeads® mRNA direct kit from Invitrogen.

In some embodiments, the nucleic acid is isolated from paraffin embedded tissue. Methods of extracting nucleic acid from paraffin embedded tissue are well known in the art e.g., paraffin blocks containing the tissue are collected, de-waxed by treatment with xylene, treated with proteinase to remove protein contaminants, and then finally extracted with phenol and chloroform, followed by ethanol precipitation. Alternatively, nucleic acid from a paraffin embedded tissue can be isolated by commercially available kits e.g., EZ1 DNA kit, QIAamp DNA Mini Kit from Qiagen; Paraffin Block RNA Isolation Kit, RecoverAll™Total Nucleic Acid Isolation Kit from Ambion.

Nucleic acid need not be extracted, but may be made available by suitable treatment of cells or tissue such as described in U.S. patent application Ser. No. 11/566,169, which is incorporated herein by reference.

Polypeptides detected in the methods of the present invention may be detected directly from a biological sample or may be further purified for detection. Any known method for polypeptide purification may be used including, but not limited to, sucrose gradient purification, size exclusion chromatography, ion exchange chromatography, affinity chromatography, immunoaffinity chromatography, HPLC, gel electrophoresis (e.g. SDS-PAGE or QPNC-PAGE), and immunoprecipitation with a BCR-ABL1 specific antibody.
Detection The bcr-abl1 polynucleotides or BCR-ABL1 polypeptides may be detected by a variety of methods known in the art. Non-limiting examples of detection methods are described below. The detection assays in the methods of the present invention may include purified or isolated DNA, RNA or protein or the detection step may be performed directly from a biological sample without the need for further DNA, RNA or protein purification/isolation.
Nucleic Acid Amplification Polynucleotides encoding bcr-abl1 can be detected by the use of nucleic acid amplification techniques which are well known in the art. The starting material may be genomic DNA, cDNA, RNA mRNA. Nucleic acid amplification can be linear or exponential. Specific variants or mutations may be detected by the use of amplification methods with the aid of oligonucleotide primers or probes designed to interact with or hybridize to a particular target sequence in a specific manner, thus amplifying only the target variant.

Non-limiting examples of nucleic acid amplification techniques include the polymerase chain reaction (PCR), reverse transcriptase polymerase chain reaction (RT-PCR), nested PCR, ligase chain reaction (see Abravaya, K., et al., *Nucleic Acids Res.* (1995), 23:675-682), branched DNA signal amplification (see Urdea, M. S., et al., *AIDS* (1993), 7(suppl 2):S11-S14, amplifiable RNA reporters, Q-beta replication, transcription-based amplification, boomerang DNA amplification, strand displacement activation, cycling probe technology, isothermal nucleic acid sequence based amplification (NASBA) (see Kievits, T. et al., *J Virological Methods* (1991), 35:273-286), Invader Technology, or other sequence replication assays or signal amplification assays.
Primers:

Oligonucleotide primers for use amplification methods can be designed according to general guidance well known in the art as described herein, as well as with specific requirements as described herein for each step of the particular methods described.

In some embodiments, oligonucleotide primers for cDNA synthesis and PCR are 10 to 100 nucleotides in length, preferably between about 15 and about 60 nucleotides in length, more preferably 25 and about 50 nucleotides in length, and most preferably between about 25 and about 40 nucleotides in length. There is no standard length for optimal hybridization or polymerase chain reaction amplification.

Methods of designing primers have been described in U.S. patent application Ser. No. 10/921,482. Primers useful in the methods described herein are also designed to have a particular melting temperature ($T_m$) by the method of melting temperature estimation. Commercial programs, including Oligo™, Primer Design and programs available on the internet, including Primer3 and Oligo Calculator can be used to calculate a $T_m$ of a polynucleotide sequence useful according to the invention.

$T_m$ of a polynucleotide affects its hybridization to another polynucleotide (e.g., the annealing of an oligonucleotide primer to a template polynucleotide). In the subject methods, it is preferred that the oligonucleotide primer used in various steps selectively hybridizes to a target template or polynucleotides derived from the target template (i.e., first and second strand cDNAs and amplified products). Typically, selective hybridization occurs when two polynucleotide sequences are substantially complementary (at least about 65% complementary over a stretch of at least 14 to 25 nucleotides, preferably at least about 75%, more preferably at least about 90% complementary). See Kanehisa, M., *Polynucleotides Res.* (1984), 12:203, incorporated herein by reference. As a result, it is expected that a certain degree of mismatch at the priming site is tolerated. Such mismatch may be small, such as a mono-, di- or tri-nucleotide. In preferred embodiments, 100% complementarity is preferred.
Probes:

Probes are capable of hybridizing to at least a portion of the nucleic acid of interest or a reference nucleic acid. Probes may be an oligonucleotide, artificial chromosome, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may be used for detecting and/or capturing/purifying a nucleic acid of interest.

Typically, probes can be about 10 nucleotides, about 20 nucleotides, about 25 nucleotides, about 30 nucleotides, about 35 nucleotides, about 40 nucleotides, about 50 nucleotides, about 60 nucleotides, about 75 nucleotides, about 100 nucleotides long.

However, longer probes are possible. Longer probes can be about 200 nucleotides, about 300 nucleotides, about 400 nucleotides, about 500 nucleotides, about 750 nucleotides, about 1,000 nucleotides, about 1,500 nucleotides, about 2,000 nucleotides, about 2,500 nucleotides, about 3,000 nucleotides, about 3,500 nucleotides, about 4,000 nucleotides, about 5,000 nucleotides, about 7,500 nucleotides, about 10,000 nucleotides long.

Probes may also include a detectable label or a plurality of detectable labels. The detectable label associated with the probe can generate a detectable signal directly. Additionally, the detectable label associated with the probe can be detected indirectly using a reagent, wherein the reagent includes a detectable label, and binds to the label associated with the probe. For example, a detectable label includes a labeled antibody or a primary antibody/secondary antibody pair, wherein the detectable label may be in the primary antibody, or in the secondary antibody or in both.

Primers or probes may be prepared that hybridize under stringent conditions to the insert sequence or to a junction sequence that includes some normal bcr-abl 1 mRNA sequence and some of the adjoining insertion sequence. Such primers or probes can be designed so that they hybridize under stringent conditions to the specific splice variant transcript but not to normal bcr-abl1 transcript. Primers or probes also can be prepared that are complementary and specific for the normal bcr-abl1 splice junction. Such primers or probes can be used to detect the normal bcr-abl1 mRNA and not the corresponding insertion mutation such as is described herein.

Primers and/or probes specific for the inserted arising from the bcr-abl1 splice variants described herein are designed to specifically hybridize to a diagnostic portion of the inserted sequence of the 195INS and 243INS variants including, for example, SEQ ID NOs: 7 and 9, respectively. Alternatively, the 195INS and 234 INS variants may be identified using primers and/or probes that are directed to the novel junctions created by the inserted sequences. Suitable primers and probes include, for example, those which contain the following nucleotide sequences (the junction is indicated by a colon):

TaqMan® probes (Heid, et al., *Genome Res* 6: 986-994, 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo)benzoic acid (DABCYL). See Tyagi, et al., 16 Nature Biotechnology 49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

| Junction Sequence | Description | SEQ ID NO: |
|---|---|---|
| ggcaag:gggag | 5' junction between exon 4 and the intron 4 insertion in the 195INS variant | 11 |
| atcagg:ctctac | 3' junction between the intron 4 insertion and exon 5 in the 195INS variant | 12 |
| tccttg:gtaggg | 5' junction between exon 6 and the intron 6 insertion in the 231INS variant | 13 |
| cccgga:gggtct | 3' junction between the intron 6 insertion and exon 7 in the 231INS variant | 14 |

Detectable Label

The term "detectable label" as used herein refers to a molecule or a compound or a group of molecules or a group of compounds associated with an oligonucleotide (e.g., a probe or primer) and is used to identify the probe hybridized to a genomic nucleic acid or reference nucleic acid.

Detectable labels include but are not limited to fluorophores, isotopes (e.g., $^{32}P$, $^{33}P$, $^{35}S$, $^{3}H$, $^{14}C$, $^{125}I$, $^{131}I$), electron-dense reagents (e.g., gold, silver), nanoparticles, enzymes commonly used in an ELISA (e.g., horseradish peroxidase, beta-galactosidase, luciferase, alkaline phosphatase), chemiluminescent compound, colorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

One general method for real time PCR uses fluorescent probes such as the TaqMan® probes, molecular beacons, and Scorpions. Real-time PCR quantifies the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

In a preferred embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes.

Suitable fluorescent moieties include but are not limited to the following fluorophores working individually or in combination: 4-acetamido-4'-isothiocyanatostilbene-2,2'disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120),7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET); fluorescamine; IR144; IR1446; lanthamide phosphors; Malachite Green isothiocyanate; 4-methylumbelliferone; ortho cresolphthalein; nitrotyrosine; pararosanilin; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; tetramethyl rhodamine isothiocyanate (TRITC).

Detection of Nucleic Acid by Size:

Methods for detecting the presence or amount of polynucleotides are well known in the art and any of them can be used in the methods described herein so long as they are capable of separating individual polynucleotides by a difference in size. The separation technique used should permit resolution of nucleic acid as long as they differ from one another by at least one nucleotide or more. The separation can be performed under denaturing or under non-denaturing or native conditions—i.e., separation can be performed on single- or double-stranded nucleic acids. Useful methods for the separation and analysis of polynucleotides include, but are not limited to, electrophoresis (e.g., agarose gel electrophoresis, capillary electrophoresis (CE)), chromatography (HPLC), and mass spectrometry.

In one embodiment, CE is a preferred separation means because it provides exceptional separation of the polynucleotides in the range of at least 10-1,000 base pairs with a resolution of a single base pair. CE can be performed by methods well known in the art, for example, as disclosed in U.S. Pat. Nos. 6,217,731; 6,001,230; and 5,963,456, which are incorporated herein by reference. High-throughput CE apparatuses are available commercially, for example, the HTS9610 High throughput analysis system and SCE 9610 fully automated 96-capillary electrophoresis genetic analysis system from Spectrumedix Corporation (State College, Pa.); P/ACE 5000 series and CEQ series from Beckman Instruments Inc (Fullerton, Calif.); and ABI PRISM 3100 genetic analyzer (Applied Biosystems, Foster City, Calif.). Near the end of the CE column, in these devices the amplified DNA fragments pass a fluorescent detector which measures signals of fluorescent labels. These apparatuses provide automated high throughput for the detection of fluorescence-labeled PCR products.

In some embodiments, nucleic acid may be analyzed and detected by size using agarose gel electrophoresis. Methods of performing agarose gel electrophoresis are well known in the art. See Sambrook et al., Molecular Cloning: A Laboratory Manual (2nd Ed.) (1989), Cold Spring Harbor Press, N.Y.

DNA Sequencing:

In some embodiments, detection of nucleic acid is by DNA sequencing. Sequencing may be carried out by the dideoxy chain termination method of Sanger et al. (*PNAS USA* (1977), 74, 5463-5467) with modifications by Zimmermann et al. (*Nucleic Acids Res*. (1990), 18:1067). Sequencing by dideoxy chain termination method can be performed using Thermo Sequenase (Amersham Pharmacia, Piscataway, N.J.), Sequenase reagents from US Biochemicals or Sequatherm sequencing kit (Epicenter Technologies, Madison, Wis.). Sequencing may also be carried out by the "RR dRhodamine Terminator Cycle Sequencing Kit" from PE Applied Biosystems (product no. 403044, Weiterstadt, Germany), Taq DyeDeoxy™ Terminator Cycle Sequencing kit (Perkin-Elmer/Applied Biosystems) using an Applied Biosystems Model 373A DNA or in the presence of dye terminators CEQ™ Dye Terminator Cycle Sequencing Kit, (Beckman 608000). Alternatively, sequencing can be performed by a method known as Pyrosequencing (Pyrosequencing, Westborough, Mass.). Detailed protocols for Pyrosequencing can be found in: Alderbom et al., Genome Res. (2000), 10:1249-1265.

Detection of Polypeptide by Size:

Methods for detecting the presence or amount of polypeptides are well known in the art and any of them can be used in the methods described herein so long as they are capable of separating polypeptides by a difference in size. The separation can be performed under denaturing or under non-denaturing or native conditions. Useful methods for the separation and analysis of polypeptides include, but are not limited to, electrophoresis (e.g., SDS-PAGE electrophoresis, capillary electrophoresis (CE)), immunoblot analysis, size exclusion chromatography, chromatography (HPLC), and mass spectrometry.

Antibody Production and Screening

Various procedures known in the art may be used for the production of antibodies which bind to variants of the BCR-ABL1 protein. Such antibodies include but are not limited to polyclonal, monoclonal, chimeric, single chain, Fab fragments and fragments produced by a Fab expression library. Antibodies that specifically bind to a diagnostic epitope of SEQ ID NOs: 5 and 6 are useful for detection and diagnostic purposes. Suitable epitopes include, for example the polypeptides encoded by SEQ ID NOs: 8 and 10.

Antibodies that differentially bind to the polypeptide of SEQ ID NOs 5 and/or 6 relative to the native BCR-ABL1 protein may also specifically detect and distinguish insertion/truncation variants of the BCR-ABL1 protein from other BCR-ABL1 proteins without such insertion/truncation mutations.

For the production of antibodies, various host animals, including but not limited to rabbits, mice, rats, etc, may be immunized by injection with the full length or fragment of variants of the BCR-ABL1 protein. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to BCR-ABL1 protein variants may be prepared by using any technique which provides for the production of antibody molecules by continuous cell lines in culture. These include but are not limited to the hybridoma technique originally described by Kohler and Milstein, (*Nature* (1975), 256:495-497), the human B-cell hybridoma technique (Kosbor et al., *Immunology Today* (1983), 4:72; Cote et al. *Proc. Natl. Acad. Sci.* (1983), 80:2026-2030) and the EBV-hybridoma technique (Cole et al., *Monoclonal Antibodies and Cancer Therapy* (1985), Alan R. Liss, Inc., pp. 77-96). In addition, techniques developed for the production of "chimeric antibodies" (Morrison et al., *Proc. Natl. Acad. Sci. USA* (1984), 81:6851-6855; Neuberger et al., *Nature* (1984), 312:604-608; Takeda et al., *Nature* (1985), 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce specific single chain antibodies which bind to variants of the BCR-ABL1 protein.

Antibody fragments which recognize variants of the BCR-ABL1 protein may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., Science. 1989; 246: 1275-1281) to allow rapid and easy identification of monoclonal Fab fragments with the desired specificity to variants of the BCR-ABL1 protein.

Antibodies to BCR-ABL1 variants can be used in a variety of techniques for detecting BCR-ABL1 polypeptides in the methods of the present invention including, but non limited to, immunoprecipitation, enzyme-linked immunosorbent assay (ELISA), protein immunoblotting techniques such as westerns, etc.

Cloning

The nucleic acid (e.g., cDNA or genomic DNA) encoding at least a portion of bcr-abl or its variants may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art, see Sambrook, et al., Molecular Cloning: A Laboratory Manual (1989), Second Edition, Cold Spring Harbor Press, Plainview, N.Y.

Prokaryotic Vectors:

Prokaryotic transformation vectors are well-known in the art and include pBlueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of *E. coli* cells include the pET expression vectors (Novagen, see U.S. Pat. No. 4,952,496), e.g., pET11a, which contains the T7 promoter, T7 terminator, the inducible *E. coli* lac operator, and the lac repressor gene; and pET 12a-c, which contain the T7 promoter, T7 terminator, and the *E. coli* ompT secretion signal. Another suitable vector is the pIN-IIIompA2 (see Duffaud et al., Meth. in Enzymology, 153:492-507, 1987), which contains the lpp promoter, the lacUV5 promoter operator, the ompA secretion signal, and the lac repressor gene.

Eukaryotic Vectors:

Exemplary, eukaryotic transformation vectors, include the cloned bovine papilloma virus genome, the cloned genomes of the murine retroviruses, and eukaryotic cassettes, such as the pSV-2 gpt system [described by Mulligan and Berg, Nature Vol. 277:108-114 (1979)] the Okayama-Berg cloning system [Mol. Cell. Biol. Vol. 2:161-170 (1982)], and the expression cloning vector described by Genetics Institute (Science. 1985; 228: 810-815), pCMV Sport, pCDNA™ 3.3 TOPO®, BaculoDirect™ Baculovirus Expression System (Invitrogen Corp., Carlsbad, Calif., USA), StrataClone™ (Stratagene, CA, USA), pBAC vectors (EMD Chemicals Inc, NJ, USA).

Vector Components:

Vector components generally include, but are not limited to, one or more of a regulatory elements such as an enhancer element, a promoter, and a transcription termination sequence, an origin of replication, one or more selection marker genes, and a cloning site.

Origin of Replication:

Both expression and cloning vectors contain a nucleic acid sequence that enables the vector to replicate in one or more selected host cells. Such sequences are well known for a variety of bacteria, yeast, and viruses. Non-limiting examples include the origin of replication from the plasmid pBR322 for most Gram-negative bacteria, the plasmid origin is suitable for yeast, and various viral origins (SV40, cytomegalovirus, polyoma, adenovirus, VSV or BPV) useful for cloning vectors in mammalian cells.

Selection Marker:

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells is those that enable the identification of cells competent to take up the bcr-abl-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA (1980), 77:4216. A suitable selection gene for use in yeast is the trp 1 gene present in the yeast plasmid YRp7 (Stinchcomb et al., Nature (1979), 282:39-43; Kingsman et al., Gene (1979), 7:141-152). The trp 1 gene provides a selection marker for a mutant strain of yeast lacking the ability to grow in tryptophan, for example, ATCC No. 44076 or PEP4-1 (Jones, Genetics (1977), 86:85-102).

Regulatory Elements:

Expression and cloning vectors usually contain a promoter and/or enhancer operably linked to the bcr-abl1 encoding nucleic acid sequence to direct mRNA synthesis. Promoters recognized by a variety of potential host cells are well known. Promoters suitable for use with prokaryotic hosts include the beta-lactamase and lactose promoter systems (Chang et al., Nature (1978), 275:617-624; Goeddel et al., Nature (1979), 281:544-548), alkaline phosphatase, a tryptophan (trp) promoter system (EP 36,776), T7 promoter, and hybrid promoters such as the tac promoter (deBoer et al., Proc. Natl. Acad. Sci. USA (1983), 80:21-25). Promoters for use in bacterial systems also will contain a Shine-Dalgarno (S.D.) sequence operably linked to the DNA encoding bcr-abl1.

Examples of suitable promoting sequences for use with yeast hosts include the promoters for 3-phosphoglycerate kinase (Hitzeman et al., J. Biol. Chem. (1980), 255:12073-12080) or other glycolytic enzymes (Holland and Holland, Biochemistry (1978), 17:4900-4907), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

bcr-abl1 transcription from vectors in eukaryotic host cells may be controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the bcr-abl1 gene by higher eukaryotes may be increased by inserting an enhancer sequence into the vector. Enhancers are cis-acting elements of DNA, usually about from 10 to 300 bp that act on a promoter to increase its transcription. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the bcr-abl1 coding sequence, but is preferably located at a site 5' from the promoter.

Vectors encoding bcr-abl1 nucleic acid sequence and its variants may further comprise non-bcr-abl1 nucleic acid sequence which may be co-expressed with bcr-abl1 and its variants either as a fusion product or as a co-transcript. Non limiting examples of such non-bcr-abl1 nucleic acid sequence includes His-tag (a stretch of poly histidines), FLAG-tag, and Green Fluorescent Protein (GFP). His-tag and FLAG-tag can be used to in many different methods, such as purification of BCR-ABL1 protein and or insertion/truncation mutant of BCR-ABL1 protein fused to such tags. The tags can also serve as an important site for antibody recognition. This is particularly important in detecting BCR-ABL1 proteins and or insertion/truncation mutant of BCR-ABL1 protein fused to such tags. GFP may be used as a reporter of expression (Phillips G. J. FEMS Microbiol. Lett. 2001; 204 (1): 9-18), such as the expression of bcr-abl1 and the splice variant of bcr-abl1.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNA or cDNA. These regions contain nucleotide segments transcribed as polyadenylated fragments in the untranslated portion of the mRNA encoding bcr-abl1.

Still other methods, vectors, and host cells suitable for adaptation to the synthesis of bcr-abl1 in recombinant vertebrate cell culture are described in Gething et al., Nature (1981), 293:620-625; Mantei et al., Nature. 1979; 281:40-46; EP 117,060; and EP 117,058.

Genetically Modifying Host Cells by Introducing Recombinant Nucleic Acid

The recombinant nucleic acid (e.g., cDNA or genomic DNA) encoding at least a portion of bcr-abl1 or its variants may be introduced into host cells thereby genetically modifying the host cell. Host cells may be used for cloning and/or for expression of the recombinant nucleic acid. Host cells can be prokaryotic, for example bacteria. Host cell can be also be eukaryotic which includes but not limited to yeast, fungal cell, insect cell, plant cell and animal cell. In preferred embodiment, the host cell can be a mammalian cell. In another preferred embodiment host cell can be human cell. In one preferred embodiment, the eukaryotic host cell may be K562 cell. K562 cells were the first human immortalized myelogenous leukemia line to be established and are a bcr-abl positive erythroleukemia line derived from a CML patient in blast crisis (Lozzio & Lozzio, Blood. 1975; 45(3): 321-334; Drexler, H. G. The Leukemia-Lymphoma Cell Line Factsbook. (2000), Academic Press.

Host cells may comprise wild-type genetic information. The genetic information of the host cells may be altered on purpose to allow it to be a permissive host for the recombinant DNA. Examples of such alterations include mutations, partial or total deletion of certain genes, or introduction of non-host nucleic acid into host cell. Host cells may also comprise mutations which are not introduced on purpose.

Several methods are known in the art to introduce recombinant DNA in bacterial cells that include but are not limited to transformation, transduction, and electroporation, see Sambrook, et al., Molecular Cloning: A Laboratory Manual (1989), Second Edition, Cold Spring Harbor Press, Plainview, N.Y. Non limiting examples of commercial kits and bacterial host cells for transformation include NovaBlue Singles™ (EMD Chemicals Inc, NJ, USA), Max Efficiency® DH5™, One Shot® BL21 (DE3) *E. coli* cells, One Shot® BL21 (DE3) pLys *E. coli* cells (Invitrogen Corp., Carlsbad, Calif., USA), XL1-Blue competent cells (Stratagene, CA, USA). Non limiting examples of commercial kits and bacterial host cells for electroporation include Zappers™ electrocompetent cells (EMD Chemicals Inc, NJ, USA), XL1-Blue Electroporation-competent cells (Stratagene, CA, USA), ElectroMAX™ *A. tumefaciens* LBA4404 Cells (Invitrogen Corp., Carlsbad, Calif., USA).

Several methods are known in the art to introduce recombinant nucleic acid in eukaryotic cells. Exemplary methods include transfection, electroporation, liposome mediated delivery of nucleic acid, microinjection into to the host cell, see Sambrook, et al., Molecular Cloning: A Laboratory Manual (1989), Second Edition, Cold Spring Harbor Press, Plainview, N.Y. Non limiting examples of commercial kits and reagents for transfection of recombinant nucleic acid to eukaryotic cell include Lipofectamine™ 2000, Optifect™ Reagent, Calcium Phosphate Transfection Kit (Invitrogen Corp., Carlsbad, Calif., USA), GeneJammer® Transfection Reagent, LipoTAXI® Trasfection Reagent (Stratagene, CA, USA). Alternatively, recombinant nucleic acid may be introduced into insect cells (e.g. sf9, sf21, High Five™) by using baculo viral vectors.

In one preferred embodiment, an exemplary vector comprising the cDNA sequence of bcr-abl splice variant (pCMV/GFP/1951NS bcr-abl) may be transfected into K562 cells. Stable transfected K 562 cells may be developed by transfecting the cells with varying amounts of the pCMV/GFP/195INS bcr-abl vector (0 ng-500 ng) using various methods known in the art. In one exemplary method, The ProFection® Mammalian Transfection System Calcium Phosphate (Promega Corporation, WI, USA) may be used. This is a simple system containing two buffers: $CaCl_2$ and HEPES-buffered saline. A precipitate containing calcium phosphate and DNA is formed by slowly mixing a HEPES-buffered phosphate solution with a solution containing calcium chloride and DNA. These DNA precipitates are then distributed onto eukaryotic cells and enter the cells through an endocytic-type mechanism. This transfection method has been successfully used by others (Hay et al. J. Biol. Chem. 2004; 279: 1650-58). The transfected K562 cells can be selected from the non-transfected cells by using the antibiotics Neomycin and Ampicillin Expression of the spliced variant of bcr-abl can assessed from the co-expression of the reporter gene GFP.

Alternatively, in a 24-well format complexes are prepared using a DNA (μg) to Lipofectamine™ 2000 (Invitrogen Corporation, Carlsbad, Calif., USA) (μl) ratio of 1:2 to 1:3. Cells are transfected at high cell density for high efficiency, high expression levels, and to minimize cytotoxicity. Prior to preparing complexes, $4-8 \times 10^5$ cells are plated in 500 ml of growth medium without antibiotics. For each transfection sample, complexes are prepared as follows: a. DNA is diluted in 50 μl of Opti-MEM® I Reduced Serum Medium without serum (Invitrogen Corporation, Carlsbad, Calif., USA) or other medium without serum and mixed gently. b. Lipofectamine™ 2000 is mixed gently before use and the mixture is diluted to appropriate amount in 50 μl of Opti-MEM® I Medium. The mixture is incubated for 5 minutes at room temperature. c. After 5 minute incubation, the diluted DNA is combined with diluted Lipofectamine™ 2000 (total volume=100 μl) and is mixed gently. The mixture is incubated for 20 minutes at room temperature. 100 μl of complexes is added to each well containing cells and medium. The contents are mixed gently by rocking the plate back and forth. Cells are incubated at 37° C. in a $CO_2$ incubator for 18-48 hours prior to testing for transgene expression. Medium may be changed after 4-6 hours. Cells are passaged at a 1:10 (or higher dilution) into fresh growth medium 24 hours after transfection. Selective medium (containing Neomycin and Ampicillin) is added the following day.

Prediction of the Likelihood of Drug Resistance in CML Patients or Subjects Suspected of Having CML Methods of the invention can be used for predicting the likelihood that a CML patient or a subject suspected of having CML with a BCR-ABL1 translocation will be resistant to treatment with one or more BCR-ABL1 kinase inhibitors. A sample from a CML patient, or a subject suspected of having CML, is assessed for the presence or absence of a polynucleotide sequence encoding the 195INS and/or the 2431NS bcr-abl1 splice variants described herein, or a complement thereof. Optionally, a sample from a CML patient, or a subject suspected of having CML, is assessed for the presence or absence of a BCR-ABL1 fusion protein having an amino acid sequence of any one of SEQ ID NOs: 5 and 6. Methods for detecting the absence or presence of such polypeptides are discussed above. The presence of the polypeptide sequence indicates that the patient has an increased likelihood of being resistant to treatment with one or more BCR-ABL1 kinase inhibitors relative to a patient not having the polynucleotide sequence. The presence of one or more of these BCR-ABL1 fusion proteins indicates that the patient has an increased likelihood of being resistant to treatment with one or more BCR-ABL1 kinase inhibitors relative to a patient not having the polynucleotide sequence.

In another embodiment, a sample from a CML patient, or a subject suspected of having CML, is assessed for the presence or absence of a polypeptide having an amino acid sequence of SEQ ID NO: 5 or 6.

Identifying a Compound for Treating Leukemic Patients

In one preferred embodiment, cell lines expressing BCR-ABL1 (both wild-type and/or mutant) proteins may be utilized to screen compounds for treating CML patients. In preferred embodiments, the compounds may be targeting BCR-ABL1 protein. In some embodiments, the compounds may be inhibitor of ABL kinase activity. Non-limiting examples of kinase inhibitors include but not limited to imatinib, dasatinib, nilotinib, Bosutinib (SKI-606) and Aurora kinase inhibitor VX-680. In other embodiments, the compounds may not be an inhibitor of ABL kinase activity.

The effect of the compounds on the cells may be assessed. Several parameters may be assessed for identifying the compounds that may be beneficial for treatment of CML patients. Non-limiting examples of the parameters that may be assessed includes cell viability, cell proliferation, apoptosis, kinase activity of BCR-ABL1 protein, additional mutations in BCR-ABL1 protein, additional mutation in ABL protein.

In one embodiment, human chronic myeloid leukemia (CML) cell lines expressing BCR-ABL1 (both wild-type and/or mutant) proteins may be used to study the effect of such compounds on their effect on the cells. Non-limiting examples of human chronic myeloid leukemia (CML) cell lines include BV173, K562, KCL-22, and KYO-1, LAMA84, EM2, EM3, BV173, AR230, and KU812 (Mahon, F. X., Blood. 2000; 96: 1070-1079; Lerma et al. Mol. Cancer Ther. 2007; 6(2): 655-66).

In other embodiments, non-CML cells may be transfected with expression vectors comprising the bcr-abl1 gene or variants of the bcr-abl1 gene including splice variants of the bcr-abl1 gene resulting in genetically modified cells comprising the recombinant polynucleotide. Thus, the transfected cells will be able to express BCR-ABL1 protein or its variants. The genetically modified cells can be used to screen compounds for treating CML patients.

In yet other embodiments, CML cell lines, for example BV173, K562, KCL-22, and KYO-1, LAMA84, EM2, EM3, BV173, AR230, and KU812 may be transfected with expression vectors comprising splice variants of bcr-abl1 gene resulting in genetically modified cells comprising the recombinant polynucleotide. The gene product of the splice variants of the bcr-abl1 gene and the insertion/truncation mutant of BCR-ABL1 may impart partial or total resistance to ABL kinase inhibitors to these genetically modified cells. The genetically modified cells may be used to screen compounds for treating CML. The compounds may be inhibitors of ABL kinase activity or these compounds may have other mechanism of action.

The CML cell lines and the genetically modified cell lines as discussed above may be grown in appropriate growth medium and using appropriate selective antibiotics. Methods for cell culture is well known in the art (Sambrook, et al., Molecular Cloning: A Laboratory Manual (1989), Second Edition, Cold Spring Harbor Press, Plainview, N.Y.). Several growth media for cell culture are commercially available. Non-limiting examples include GIBCO® RPMI Media 1640, Dulbecco's Modified Eagle Medium (DMEM), DMEM: Nutrient Mixture F-12 (DMEM/F12), Minimum Essential Media (Invitrogen Corp., Carlsbad, Calif., USA), RF-10 medium. Non-limiting examples of selective antibiotics include ampicillin, neomycin, Geneticin®, Hygromycin B.

In one preferred embodiment, K562 cells (ATCC catalog no: CCL-243) may be genetically modified by transfecting with different amounts of the expression vector pCMV/GFP/195INS bcr-abl or pCMV/GFP/243INS bcr-abl. In one embodiment, the amount the expression vector used for transfection can be 0 ng, or can be at least about: 1 ng, 2 ng, 5 ng, 7.5 ng, 10 ng, 12.5 ng, 15 ng, 20 ng, 25 ng, 30 ng, 40 ng, 50 ng, 60 ng, 75 ng, 100 ng, 125 ng, 200 ng, 500 ng, 750 ng, or 1 µg. The transfected cells may be grown in RF-10 medium with neomycin/and or ampicillin Assessing the Effect of a Compound for Treatment of Leukemia on Genetically Modified Cells Several parameters may be assessed for identifying the compounds that may be beneficial for treatment of CML patients. Non-limiting examples of the parameters that may be assessed includes cell viability, cell proliferation, apoptosis, kinase activity of BCR-ABL1 protein, additional mutations in BCR-ABL1 protein, and additional mutation in the ABL protein.

Cell Viability:

Cells can be plated at a density of $2-2.5\times10^5$ cells/mL in RF-10 with varying amounts of the compound or without the compound. Aliquots are taken out at 24-hour intervals for assessment of cell viability by trypan blue exclusion.

Alternatively, cell viability can be measured by colorimetric assay such as MTT assay (Mosman et al. J. Immunol. Meth. 1983; 65: 55-63). Commercial kits for MTT assay are available. For example, CellTiter 96® Non-Radioactive Cell Proliferation Assay (MTT) (Promega Corporation, WI, USA), Vybrant® MTT Cell Proliferation Assay Kit (Invitrogen Corp., Carlsbad, Calif., USA).

Cell Proliferation:

Proliferation of the genetically modified cells in presence of a compound for treatment of CML patient can be measured in several ways. The proliferation of the cells can be indicative of the effectiveness of the compound for CML therapy.

In one such method, cell proliferation assay can performed using MTS tetrazolium such as Cell Titer96 Aqueous (Promega corporation, WI, USA), which measures numbers of viable cells. Between $2\times10^3$ and $2\times10^4$ cells are washed twice in RF-10 and plated in quadruplicate into microtiterplate wells in 100 µL RF-10 plus various doses of the compound. Controls using the same concentrations of compound without cells are set up in parallel. Twenty microliters MTS is added to the wells at daily intervals. Two hours after MTS is added, the plates are read in a microplate auto reader (Dynex Technologies, Billingshurst, UK) at 490-nm wavelength. Results are expressed as the mean optical density for each dose of the compound. All experiments are repeated at least 3 times.

In another method, cell proliferation assays can be performed by monitoring the incorporation bromo-deoxyuracil (BrdU) into newly synthesized DNA. The Amount of BrdU incorporated into the DNA will be proportional to the amount of DNA synthesis and will be indicative of the proliferating cells. In one such method, detectably labeled anti-BrdU antibody can be used to measure the amount of BrdU incorporated into the cells treated with various amounts of the compound. In one embodiment, the detectable label can be FITC. The amount of signal from FITC-labeled anti-BrdU bound to the DNA can be measured by Flow Cytometry. Commercially available kits for flow cytometry based cell proliferation assays are available. Such as, Click-iT® EdU (Invitrogen Corp., Carlsbad, Calif., USA). ELISA based assays for measuring BrdU incorporation by proliferating cells care commercially available examples include BrdU Cell Proliferation Assay kit (Calbiochem, EMD Chemicals Inc, NJ, USA).

In another method, proliferation of cells treated with various amounts of the compound can be measured by monitoring the incorporation of radioactively labeled deoxynucleotides (Sun et al. Cancer Res. 1999; 59: 940-946).

Kinase Activity of BCR-ABL1:

The effect of a compound on the kinase activity of the BCR-ABL1 protein is assessed by monitoring tyrosine phosphorylation profile of the cellular proteins. CrkL is a substrate of BCR-ABL1 tyrosine kinase (Ren et al. Genes Dev. 1994; 8(7): 783-95). Genetically modified cells comprising recombinant bcr-abl or variant so of bcr-abl including the splice variant are grown in presence of various amounts of a compound for treating CML patients. In a preferred embodiment, the compounds are ABL tyrosine kinase inhibitors. Non-limiting examples of kinase inhibitors include imatinib, nilotinib, dasatinib, Bosutinib (SKI-606) and Aurora kinase inhibitor VX-680. Amount of phosphorylated CrkL protein can be measured by using detectably labeled anti-phospho CrkL antibody. In one embodiment, the detectable label is phycoerythrin. The signal can be detected by flow cytometer. Alternatively, the signal can be detected by Fluorescent Microtiter plate reader.

Sequencing of the ABL Kinase Domain:

To further investigate the reason for some cells that do not overexpress BCR-ABL1 but that have higher resistance to a compound that target the ATP-binding site of the ABL kinase domain (such as imatinib, nilotinib, dasatinib, and Aurora kinase inhibitor VX-680) than their sensitive counterparts, the entire kinase domain of K562-sensitive and -resistant cells can be sequenced. Sequencing can be performed using ABI prism 377 automated DNA sequencer (PE Applied Biosystems; USA). Sequence analysis can performed using the GCG version 10 software.

In summary, 195INS BCR-Abl and 243INS bcr-abl1 variants described herein are created by an exonic insertion of a sequence from the adjacent preceding intron and produce an exclusively-expressed splicing variant in the absence of wild-type bcr-abl1 transcript. The 195INS variant causes early translational termination and truncation of the BCR-ABL1 protein missing a significant portion of the C-terminal regulatory region and is associated with significant drug resistance not only to imatinib, but also to one or more of the newer tyrosine kinase inhibitors—nilotinib and dasatinib. The 243 INS variant results in a non-native 81 amino acid insertion which may result in resistance to tyrosine kinase inhibitors. The invention will now be described in greater detail by reference to the following non-limiting examples.

EXAMPLE 1 bcr-abl1 Mutation Detection and Analysis

Venous blood was collected from a CML patient who was resistant to more than one of the three kinase inhibitors: imatinib, nilotinib and dasatinib. The bcr-abl1 allele was amplified from the blood sample in a first round one step RT-PCR. A forward primer that anneals at bcr exon b2 (BCR F; SEQ ID NO: 15) and a reverse primer (ABL-R2; SEQ ID NO: 16) that anneals at the junction of abl exons 9 and 10 were used in first round PCR to ensure that the normal, non-translocated abl gene would not be analyzed.

The ABL kinase domain was then amplified in semi-nested PCR followed by direct sequencing using ABI/prism Big-Dye terminator cycle sequencing kit on automated capillary DNA sequencer (ABI Prismt® 3100 Genetic Analyzer). The nested PCR amplified the region encoding the entire BCR-ABL tyrosine kinase domain and the activation loop using a forward primer that anneals to exon 4 (ABL-F1; SEQ ID NO: 17) and a reverse primer that anneals to the junction of abl exon 9 and 10 (ABL-R2; SEQ ID NO: 16). The resulting fragment was gel extracted, purified and sequenced in both forward and reverse directions using SEQ ID NOs: 16, 17, 18, and 19. Sequencing data were base-called by Sequencing Analysis software and assembled and analyzed by ABI Prism® SeqScape software using GenBank accession number M14752 as a reference. Primer sequences for the first and second rounds of PCR are listed below.

```
SEQ ID NO: 15    TGA CCA ACT CGT GTG TGA AAC TC
SEQ ID NO: 16    TCC ACT TCG TCT GAG ATA CTG GAT T
SEQ ID NO: 17    CGC AAC AAG CCC ACT GTC T
SEQ ID NO: 18    CAA GTG GTT CTC CCC TAC CA
SEQ ID NO: 19    TGG TAG GGG AGA ACC ACT TG
```

EXAMPLE 2 bcr-abl1 195INS and 243INS Splice Variants

Two mutations, resulting from alternative splicing in the ABL1 kinase domain, were detected in kinase resistant CML patients. The two splice variants, 195INS and 243INS both resulted in frameshift mutations. FIG. 1 shows the mRNA sequence for the human abl1 gene, which is the gene region in the bcr-abl1 translocation affected by these mutations. FIG. 2 shows the amino acid sequence for human ABL1 protein, which is the part of the BCR-ABL1 fusion protein that is changed in these mutations.

The 195INS splice variant carries an insertion of a 195 nucleotide sequence in the abl1 exon 4-5 junction at position 553 in FIG. 1. The 195 nucleotide sequence is derived from intron 4 of the abl1 gene. FIG. 3 shows the altered nucleotide sequence of the abl1 mRNA with the insertion underlined. The resulting amino acid sequence of the ABL1 portion of the BCR-ABL1 fusion protein changes at amino acid 184 and truncates at amino acid 187 in the ABL1 sequence shown in FIG. 2. FIG. 5A shows the amino acid sequence of the ABL1 portion of the BCR-ABL1 protein with the differing amino acids underlined. This particular patient shows no additional mutations in the ABL1 kinase domain.

The 243INS splice variant carries an insertion of a 243 nucleotide sequence in the abl1 exon 6-7 junction at position 911 in FIG. 1. The 243 nucleotide sequence is derived from intron 6 of the abl1 gene. The altered nucleotide sequence of the abl1 mRNA is shown in FIG. 4, with the 243 bp insertion underlined. The resulting amino acid sequence of the ABL1 portion of the BCR-ABL1 fusion protein acquires an additional 81 amino acids starting at amino acid 304 of in the ABL1 sequence shown in FIG. 2. The altered ABL1 protein does not truncate early. The amino acid sequence of the altered ABL1 portion of the BCR-ABL1 protein is shown in FIG. 5B, with the differing amino acids underlined. This particular patient shows no additional mutations in the ABL1 kinase domain.

Approximately 40-60% of human genes undergo alternative splicing, and alterations in alternative splicing have been manifested by its clinical connections to many human diseases, including cancers (Caceres & Kornblihtt, *Trends in Genetics* 2002 18:186-93; Stoilov et al., *DNA and Cell Biol.* 2002 21:803-18; Wu et al., "Alternatively Spliced Genes," In *Encyclopedia of Molecular and Cell Biology and Molecular Medicine*, Vol. 1, 2$^{nd}$ ed., 125-177 (2004)). Alternative splicing mutations in patients with CML being treated with tyrosine kinase inhibitors could be an overlooked mechanism for the resistance to therapy. Two alternative splicing mutations, 195INS and 234INS, were detected in multidrug resistant CML patients, in which they are the only isoform of bcr-abl1 transcript to be detected.

In summary, each of the two splicing variants described herein 1) are created by an exonic insertion of a sequence from the adjacent preceding intron; and 2) are associated with significant drug resistance not only to imatinib, but also to one or more of the newer tyrosine kinase inhibitors—nilotinib and dasatinib. These 2 identified mutations, along with the previously reported 35INS (Lee et al.), appear to be a part of a new class of alternative splicing mutations.

Unless otherwise defined, all technical and scientific terms used herein have the same meaning as commonly understood by one of ordinary skill in the art to which this invention belongs. All nucleotide sequences provided herein are presented in the 5' to 3' direction.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method of detecting the presence of a nucleic acid encoding a 195-INS bcr-abl splice variant in a sample comprising bcr-abl nucleic acids, comprising contacting the sample with a labeled nucleic acid probe that hybridizes to the 5' junction site or the 3' junction site of the intron 4 insertion in the 195-INS bcr-abl splice variant and detecting the hybridized labeled nucleic acid probe to detect the bcr-abl splice variant.

2. The method of claim 1, wherein the sample is a biological sample obtained from a patient diagnosed with a myeloproliferative disease.

3. The method of claim 1, wherein the sample comprises blood cells.

4. The method of claim 3, wherein the sample comprises peripheral blood mononuclear cells (PBMCs).

5. The method of claim 1, wherein the sample comprises mRNA.

6. The method of claim 1, wherein the sample comprises cDNA.

7. The method of claim 1, wherein the labeled nucleic acid probe has a sequence selected from the group consisting of SEQ ID NOs: 11 and 12.

8. The method of claim 7, wherein the labeled nucleic acid probe hybridizes to mRNA in the sample.

9. The method of claim 7, wherein the labeled nucleic acid probe hybridizes to cDNA in the sample.

10. The method of claim 1, wherein the detection assay comprises amplifying at least a portion of a nucleic acid encoding the 195-INS bcr-abl splice variant.

11. The method of claim 10, wherein said amplifying comprises performing polymerase chain reaction with primers directed to a nucleic acid sequence encoding the 195-INS bcr-abl splice variant.

* * * * *